(12) United States Patent
Caldwell et al.

(10) Patent No.: US 8,072,584 B2
(45) Date of Patent: *Dec. 6, 2011

(54) OPTICAL AIR DATA SYSTEMS AND METHODS

(75) Inventors: Loren M. Caldwell, Ft. Collins, CO (US); Shoou-yu Tang, Ft. Collins, CO (US); Phillip E. Acott, Ft. Collins, CO (US); Lisa G. Spaeth, Littleton, CO (US); Martin O'Brien, Conifer, CO (US)

(73) Assignee: Ophir Corporation, Littleton, CO (US)

( * ) Notice: Subject to any disclaimer, the term of this patent is extended or adjusted under 35 U.S.C. 154(b) by 463 days.

This patent is subject to a terminal disclaimer.

(21) Appl. No.: 12/138,163

(22) Filed: Jun. 12, 2008

(65) Prior Publication Data

US 2010/0195100 A9    Aug. 5, 2010

Related U.S. Application Data

(63) Continuation-in-part of application No. 11/488,259, filed on Jul. 17, 2006, now Pat. No. 7,564,539, which is a continuation-in-part of application No. 11/103,020, filed on Apr. 11, 2005, now Pat. No. 7,400,385, which is a continuation of application No. 10/632,735, filed on Aug. 1, 2003, now Pat. No. 6,894,768.

(60) Provisional application No. 60/699,630, filed on Jul. 15, 2005, provisional application No. 60/400,462, filed on Aug. 2, 2002.

(51) Int. Cl.
*G01P 3/36* (2006.01)
*G01N 21/00* (2006.01)

(52) U.S. Cl. ............... 356/28.5; 356/28; 356/342
(58) Field of Classification Search ............ 356/28, 356/28.5, 337, 342
See application file for complete search history.

(56) References Cited

U.S. PATENT DOCUMENTS

| 4,483,614 A | 11/1984 | Rogers |
| 4,988,190 A | 1/1991 | Miles |
| 5,111,055 A | 5/1992 | Fima |
| 5,267,010 A | 11/1993 | Kremer et al. |
| 5,285,256 A | 2/1994 | Nelson et al. |

(Continued)

FOREIGN PATENT DOCUMENTS

EP   1158300   11/2001

(Continued)

OTHER PUBLICATIONS

U.S. Appl. No. 11/488,259, Response to Office Action filed Feb. 16, 2009; 11 pages.

(Continued)

*Primary Examiner* — Isam Alsomiri
(74) *Attorney, Agent, or Firm* — Lathrop & Gage, LLP

(57) ABSTRACT

Systems and methods for sensing air includes at least one, and in some embodiments three, transceivers for projecting the laser energy as laser radiation to the air. The transceivers are scanned or aligned along several different axes. Each transceiver receives laser energy as it is backscattered from the air. A computer processes signals from the transceivers to distinguish molecular scattered laser radiation from aerosol scattered laser radiation and determines air temperatures, wind speeds, and wind directions based on the scattered laser radiation. Applications of the system to wind power site evaluation, wind turbine control, traffic safety, general meteorological monitoring and airport safety are presented.

44 Claims, 14 Drawing Sheets

U.S. PATENT DOCUMENTS

| | | | |
|---|---|---|---|
| 5,394,238 | A | 2/1995 | Mocker et al. |
| 5,835,252 | A | 11/1998 | Meier et al. |
| 6,307,626 | B1 | 10/2001 | Miles et al. |
| 6,512,996 | B1 | 1/2003 | Praskovsky et al. |
| 7,106,447 | B2 | 9/2006 | Hays |
| 7,400,385 | B2 * | 7/2008 | Caldwell et al. ............ 356/28 |
| 7,564,539 | B2 * | 7/2009 | Caldwell et al. ............ 356/28.5 |
| 7,760,339 | B2 * | 7/2010 | Caldwell et al. ............ 356/28.5 |
| 2004/0027570 | A1 | 2/2004 | Caldwell et al. |
| 2004/0263826 | A1 | 12/2004 | Langdon |
| 2006/0140764 | A1 | 6/2006 | Smith et al. |
| 2007/0109528 | A1 | 5/2007 | Caldwell et al. |
| 2009/0046289 | A1 | 2/2009 | Caldwell et al. |
| 2009/0051896 | A1 | 2/2009 | Caldwell et al. |

FOREIGN PATENT DOCUMENTS

| | | |
|---|---|---|
| WO | WO9935519 | 7/1999 |
| WO | WO2004077067 | 9/2004 |

OTHER PUBLICATIONS

U.S. Appl. No. 11/488,259, Notice of Allowance dated Apr. 16, 2009, 4 pages.
U.S. Appl. No. 11/488,259, Issue Fee Payment dated Jun. 16, 2009, 1 page.
European Application No. 09160572.5 Search Report, Sep. 25, 2009, 5 pages.
Canadian Application 2,494,458 Notice of Allowance dated Feb. 20, 2009, 1 page.
U.S. Appl. No. 12/140,186 Office Action mailed Jul. 22, 2009, 8 pages.
U.S. Appl. No. 12/140,186 Response to Office Action filed Oct. 22, 2009, 16 pages.
U.S. Appl. No. 12/140,186, Notice of Allowance mailed Mar. 9, 2010, 6 pages.
U.S. Appl. No. 12/140,186, Examiner Interview Summary mailed Jan. 22, 2010, 3 pages.
U.S. Appl. No. 12/140,186, Response to Interview Summary and Notice of Incomplete Reply filed Jan. 22, 2010, 11 pages.
Grinstead, J.H., et al "Frequency-Modulated Filtered Rayleigh Scattering (FM-FRS): A New Technique for Real-Time Velocimetry" paper 96-0302, American Institute of Aeronautics and Astronautics, Inc., pp. 1-11, 1996.
ed.Boutier, A New Trends in Instrumentation for Hypersonic Research, Seasholtz, R. G. 1993: "2D Velocity and Temperature Measurements in High Speed Flows Based on Spectrally Resolved Rayleigh Scattering", Advanced Research NATO Workshop, ONERA, Le Fauga-Muazac, France, Apr. 27-May 1, 399-408.
Kliner, D. A. V., et al,; 2002: "Efficient Second, Third, Fourth, and Fifth Harmonic Generation of Yb-Doped Fiber Amplifier", Optics Communications, 210, 393-398.
Korb, C.L.; Gentry, B. M.; Weng, C.Y. 1992: "Edge Technique: Theory and Application to the Lidar Measurement of Atmospheric Wind," Applied Optics, 31, 4202.
Miles, R. B.; et al., 1992: "Filtered Rayleigh Scattering Measurements in Supersonic/Hypersonic Facilities", AIAA 17th Aerospace Ground Testing Conference, paper AIAA-92/3894, pp. 1-10.
Philippe, L. C. & Hanson, R.K. 1993: "Laser Diode Wavelength-Modulation Spectroscopy for Simultaneous Measurement of Temperature, Pressure, and Velocity in Shock-Heated Oxygen Flows", Applied Optics, 32, 6090-6103.
She, C. Y.,et al.; 1992: "High Spectral-Resolution Rayleigh-Mie Lidar Measurment of Aerosol and Atmospheric Profiles", Optics Letters, 17, 541.
Shimizu, H. et al., "High spectral resolution lidar system with atomic blocking filters for measuring atmospher parameters," Applied Optics 22, 1372-1381 (1983).
Wu, Y., et al.; 1995: "New Method for Acquiring a High-Resolution Atomospheric Rayleigh-Mie Spectrum", Optical Engineering, Apr., 34, No. 4, 1195-1199.
Yalin, A.P. & Miles, R. B. 1999: "Ultraviolet Filtered Rayleigh Scattering Temperature Measurements with a Mercury Filter", Optics Letters, 24, 590-592.
Tenti, G., et al., 1974: "On the Kinetic Model Description of Rayleigh-Brillouin Scattering From Molecular Glasses", Canadian Journal of Physics, 52, 285-290.
Alvarez II, R. J., et al., 1993: "Profiling Temperature, Pressure, and Aerosol Properties Using a High Spectral Resolution Lidar Employing Atomic Blocking Filters", Journal of Atmospheric and Oceanic Technology, 10, 546.
PCT Application No. PCT/US03/24191; International Search Report dated Mar. 17, 2004, 7 pages.
U.S. Appl. No. 10/632,735; selected pages from Image File Wrapper; Nov. 12, 2003 through Apr. 24, 2007; 40 pages.
U.S. Appl. No. 11/103,020; selected pages from Image File Wrapper; May 17, 2007 through Jun. 25, 2007; 57 pages.
U.S. Appl. No. 11/488,259; Restriction Requirement mailed Jun. 27, 2008; 7 pages.
U.S. Appl. No. 11/488,259; Response to Restriction Requirement; filed Jul. 28, 2008; 5 pages.
U.S. Appl. No. 11/488,259; Office Action mailed Nov. 14, 2008; 8 pages.
Canadian Application 2,494,458, Office Action dated Feb. 5, 2008.
Canadian Application 2,494,458, Response to Office Action filed Aug. 5, 2008.
European Application EP 03 749 002.6, Letter and formal drawings; Feb. 11, 2005; 12 pages.
European Application EP 03 749 002.6, Amendment; Mar. 10, 2005, 14 pages.
European Application EP 03 749 002.6, Amendment; Apr. 13, 2005; 9 pages.
European Application EP 03 749 002.6, Examination Report dated Mar. 2, 2006; 6 pages.
European Application EP 03 749 002.6, Reply to Examination Report filed Aug. 25, 2006; 36 pages.
European Application EP 03 749 002.6, Invitation Pursuant to Article 96(2) and Rule 51(2); Consultation by Telephone; Nov. 17, 2006; 3 pages.
European Application EP 03 749 002.6, Result of Consultation by Telephone and copy of Form 2036; Nov. 24, 2006; 2 pages.
European Application EP 03 749 002.6, Communication about intention to grant a European patent; Dec. 8, 2006; 6 pages.
European Application EP 03 749 002.6, Letter dated Mar. 15, 2007; 1 page.
European Application EP 03 749 002.6, Decision to Grant a European Patent, Apr. 5, 2007; 2 pages.

* cited by examiner

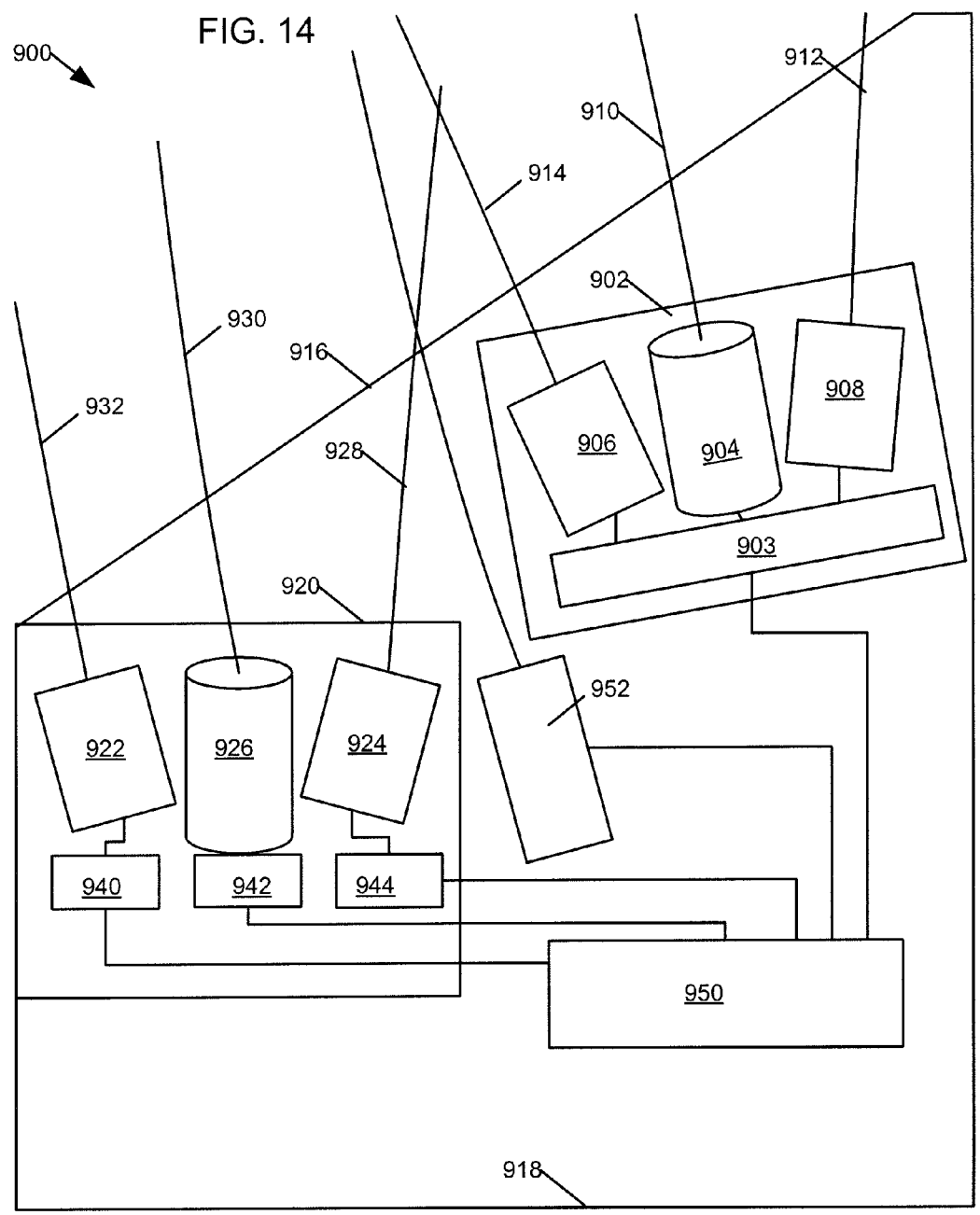

OPTICAL AIR DATA SYSTEMS AND METHODS

CROSS-REFERENCE TO RELATED APPLICATIONS

This application claims benefit of priority to and is a continuation-in-part of commonly-owned and copending U.S. patent application Ser. No. 11/488,259. In turn, U.S. patent application Ser. No. 11/488,259 claims benefit of priority to U.S. Provisional Patent Application Ser. No. 60/699,630 filed Jul. 15, 2005. This application is also a continuation-in-part of U.S. application Ser. No. 11/103,020 filed 11 Apr. 2005, which is a continuation of U.S. application Ser. No. 10/632,735 filed Aug. 1, 2003, now U.S. Pat. No. 6,894,768, which claims benefit of priority to U.S. Provisional Patent Application No. 60/400,462 filed Aug. 2, 2002. All of the aforementioned applications are hereby incorporated by reference.

U.S. GOVERNMENT RIGHTS

This invention was made in part with the support of the U.S. Government; the U.S. Government has certain rights in this invention as provided for by the terms of Grant #NAS4-02043 awarded by the NASA Dryden Flight Research Center.

BACKGROUND

An Air Data System ("ADS") provides sensed telemetry informing pilots, navigators or Vehicle Management System computers of air parameter(s) affecting aircraft stability. These air parameters include, for example, air speed, air temperature and air pressure, each being useful for navigation and flight control. The ADS exists in many forms, for example, as mechanical, opto-mechanical or opto-electronic devices.

An Optical Air Data System ("OADS") uses light to determine parameters of air speed. The OADS transmits light pulses into the atmosphere and receives light that aerosols reflect or "backscatter" towards the aircraft. Aerosols are fine solids and/or liquid particles suspended in air or other gases. The OADS may also measure the Doppler effect by receiving backscattered light and measuring its return frequency to determine speed. Certain prior art OADSs rely on scattered light that is unpredictable because of aerosol distributions that vary significantly with altitude and cloud content. In addition, some regions of the atmosphere contain too few aerosols to enable reliable air data measurements, and such an OADS cannot determine air temperature or air pressure.

Ground-based air data measurements can also be of interest in other applications such as wind measurements for weather monitoring, weather prediction and traffic alerts.

Wind conditions near airports and on approach paths to airports can be of great interest to pilots. In particular, improved detection and measurement of wind shear, updraft, downdraft, and microburst conditions has been of interest since a microburst was blamed for the demise of a Lockheed L-1011 trying to land at Dallas in 1985. Aircraft are particularly sensitive to such wind conditions during the critical flight phases of takeoff and landing; it is desirable to equip airports with devices for detecting such conditions so that destruction of aircraft and death of crew and passengers can be avoided.

Wind conditions are often measured at more than one point on an airport in an attempt to detect potentially harmful wind conditions. Since wind shear is characterized by a difference in wind speeds and directions with altitude, it is also desirable to measure wind conditions at several altitudes and not just near the surface.

Tax and other incentives enacted by the United States and several states have increased interest in obtaining electric power from renewable energy sources, including wind power systems. Detailed measurements of wind speed, air temperature, air turbulence, and similar information at the surface and at altitudes within a few hundred meters of the surface are of use in evaluating locations for wind power systems. Further, realtime measurements of wind conditions, turbulence, and temperature at the surface and at altitude may be of use in controlling wind power systems and in predicting updrafts and microbursts to help protect such systems from adverse conditions.

SUMMARY

A method for sensing air includes using at least one, and at times three, transceivers for projecting laser energy as laser radiation to the air. When using three transceivers, the transceivers are aligned along several different axes, when using one transceiver the projected radiation may be scanned. Each transceiver receives laser energy as it is backscattered from the air. A computer processes signals from the one or more transceivers to distinguish molecular scattered laser radiation from aerosol scattered laser radiation and determines air temperatures, wind speeds, and wind directions based on the scattered laser radiation. Applications of the method to wind power site evaluation, wind turbine control, weather monitoring, aircraft air data sensing, and airport safety are presented. In some embodiments the laser energy is scanned to cover a region of interest.

A system for optically sensing air data has a tunable laser for generating laser radiation and a beam splitter for splitting the laser radiation into a projected component and a control component. A control component detector receives at least a portion of the control component through an optical notch filter and generates an electronic control signal. The projected component is emitted into the air and a portion of scattered radiation is received as backscattered radiation, a portion of which is received through an optical notch filter into a backscattered radiation detector to generate an electronic backscatter signal therefrom. The wavelength of the tunable laser is swept and the control signal and backscatter signal are compared to determine Doppler shift, this is used to determine wind speed. In an embodiment, a pseudorandom sequence generator modulates the laser radiation and the electronic backscatter signal is correlated with the random sequence to determine the Doppler shift at several ranges from the system.

BRIEF DESCRIPTION OF THE DRAWINGS

FIG. 14 illustrates an alternative embodiment of the ground-based air data system.

DETAILED DESCRIPTION OF THE EMBODIMENTS

Figure 1:
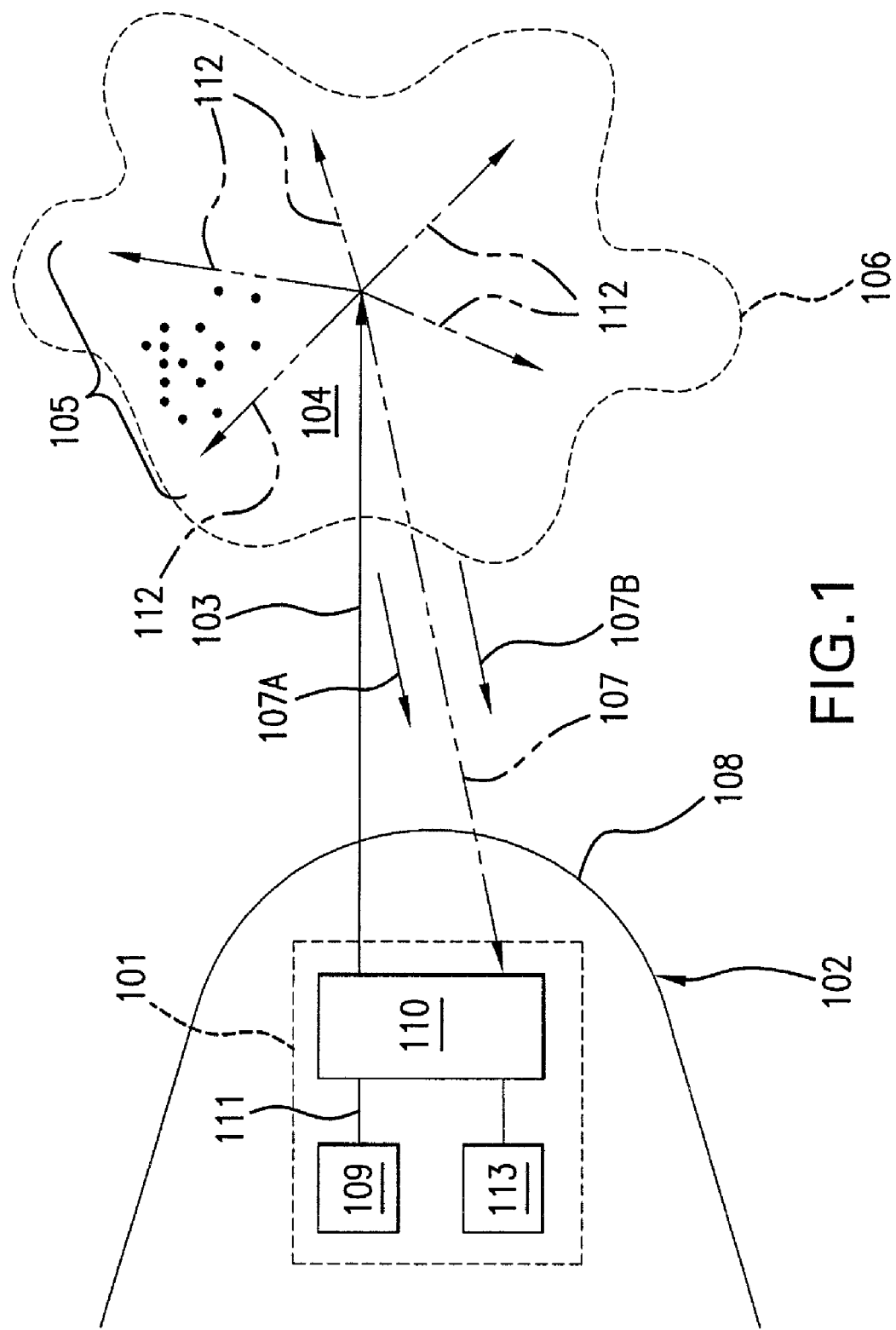
FIG. 1 shows one Optical Air Data System ("OADS"), according to an embodiment.

FIG. 1 shows one Optical Air Data System ("OADS") 101 mounted on or within an aircraft 102. In this embodiment, OADS 101 is configured for projecting laser radiation 103 to air 104. Laser radiation 103 impinges on air 104 and aerosol particles 105 (in air 104), causing scattering of laser radiation 103, which is represented in FIG. 1 as a scatter field 106. Distance between aircraft 102 and scatter field 106 is controlled by overlap between laser radiation 103 and the transceiver 110 field of view at a distance from aircraft 102, to provide an optimized intensity for return laser radiation 107 and to eliminate possible measurement error arising from displaced air proximate to aircraft 102. OADS 101 detects backscattered laser radiation 107 that is backscattered from air 104 at laser scatter field 106. Radiation 107 may be in the ultra-violet (UV) spectrum, for example, having a wavelength within a range of 250 nm to 270 nm; however, other ranges may alternatively be used to produce scatter field 106.

Return laser radiation 107 typically contains molecular scattered (e.g., Rayleigh) components 107A and/or aerosol scattered (e.g., Mie) components 107B. OADS 101 distinguishes the molecular scattered components 107A from the aerosol scattered components 107B and correspondingly determines one or more air parameters based on backscattered laser radiation 107. Examples of such air parameters include air speed, air pressure, air temperature and/or aircraft orientation angles relative to the local wind. OADS 101 may be configured with other aircraft as well, including unmanned air vehicles (UAVs), helicopters, missiles, gliders and space shuttles. Although illustrated within a "nose" 108 of aircraft 102, OADS 101 may be configured in any other part of aircraft 102.

As shown in FIG. 1, OADS 101 includes a laser 109 configured for generating laser radiation 103. Transceiver 110 is configured for transmitting laser radiation 103, from laser 109 via optical coupling 111, and receiving backscattered laser radiation 107. Optical coupling 111 may exist in the form of a fiber optic connection or free space transmission. Accordingly, transceiver 110 projects the laser radiation as laser radiation 103 to air 104. Air 104 scatters laser radiation 103 at scatter field 106 in a plurality of directions (e.g., illustrated as vectors 112). Scatter field 106 also returns, or backscatters, radiation 107 towards transceiver 110, which subsequently receives the backscattered laser radiation 107. Transceiver 110 converts backscattered laser radiation 107 to processable electronic signals, via computer 113, to determine the air parameters.

Computer 113 communicatively couples with transceiver 110 and processes signals from transceiver 110 to distinguish a molecular-scattered component 107A from an aerosol-scattered component 107B. Computer 113 determines the air parameters based on laser radiation 107 backscattered from molecules and/or aerosols in air 104. Accordingly, as described below, computer 113 may employ one or more digital signal processing algorithms to determine such parameters.

While OADS 101 illustrates one transceiver 110 in an exemplary embodiment, a plurality of transceivers may be used, depending on an application. For example, a missile employing OADS 101 may use two transceivers 110 to determine air parameters such as a forward velocity (e.g., air speed) and a vertical plane, or angle of attack, of the missile. An airplane may use three transceivers 110 positioned in a particular manner to determine various aircraft geometries, such as angle of attack and sideslip, in addition to the air parameters of air speed, air pressure and air temperature. In addition, air vehicles (fixed wing and rotary) may employ three or more transceivers and/or lasers to increase Optical Air Data System reliability through redundant system architecture. Using three OADS transceivers mounted on three non-coplanar axes may fully resolve a total airspeed vector by providing three independent measurements for the air speed vector. The transceivers are for example located in uncommon planes and their geometry known respective of an aircraft centerline. Vector algebra may then be used to determine the full airspeed vector, including forward air speed, angle-of-sideslip and angle-of-attack.

Figure 2:
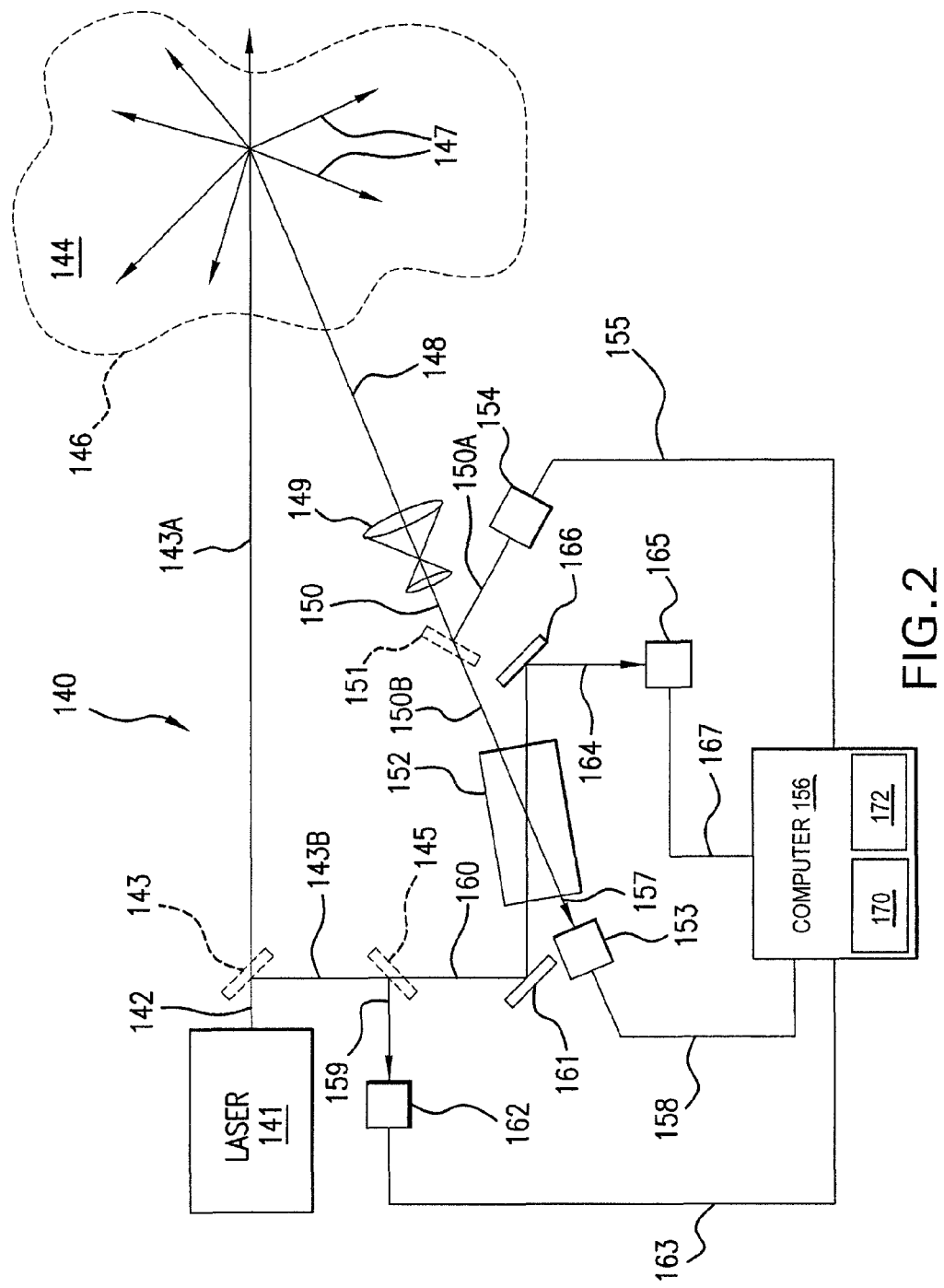
FIG. 2 shows one OADS, according to an embodiment.

FIG. 2 shows one OADS 140. OADS 140 illustrates another embodiment used for determining air parameters, such as those described in FIG. 1, based upon laser radiation backscattered from both air molecules and aerosols. In this embodiment, OADS 140 includes laser 141 configured for generating laser radiation 142. Laser 141 may be a tunable laser having a tuned center wavelength of about 253.7 nm, although other wavelengths may be used. For example, laser 141 may be a frequency quadrupled, Nd:YAG (i.e., neodymium:yttrium-aluminum-garnet) pumped Ti:Sapphire (titanium-sapphire) laser. Alternatively, frequency-quadrupled Yb-doped (ytterbium-doped) fiber lasers may be used that offer important benefits of smaller size, lighter weight, increased robustness and improved reliability, as compared to Nd:YAG-pumped Ti:Sapphire lasers. Alternately, diode lasers, diode laser bars, stacks of diode laser bars and frequency up-conversion techniques can be used to fabricate the laser. Laser 141 may generate laser radiation that is tunable across a frequency range of about 40 GHz; laser 141 may be a continuous wave laser, which sweeps in frequency across this range, or it may be a pulsed laser controlled such that each pulse has a frequency distribution centered about a tunable peak frequency. In one embodiment, the peak frequency increments by about 100 MHz from each pulse to the next. Laser 141 may tune +/−20 GHz about a center frequency of approximately 1182.5 THz, or c/253.7 nm, where c is the speed of light (approximately $3 \times 10^8$ m/s). In the illustrated embodiment, laser 141 radiates laser radiation 142 to beam splitter 143, which splits the beam into two components, 143A and 143B. Component 143A is directed through air 144; component 143B is directed to beam splitter 145.

In particular, component 143A of laser radiation 142 directed to air 144 is scattered into scatter field 146. Scattering of component 143A is illustrated by scattering vectors 147 in scatter field 146, whereas return scattering is illustrated by backscattered laser radiation 148. Component 143B of the laser radiation 142 is used as a reference for comparison to backscattered laser radiation 148. Such a comparison is for example useful in determining air parameters such as air speed, since transmitted and received frequencies of the laser radiation may be ascertained for use in a Doppler equation; such a process is explained in greater detail herein below.

In the illustrated embodiment, backscattered laser radiation 148 is received through optics 149. In one example, optics 149 is a telescope that gathers backscattered laser radiation 148 into a beam 150. Optics 149 also directs beam 150 to beam splitter 151, to split beam 150 into two components 150A/150B. Component 150B of beam 150 passes through vapor filter 152 to detector 153 to produce electronic signal 158 representative of the component 150B impinging detector 153; whereas component 150A is directed by beam splitter 151 to detector 154.

In one embodiment, detector 154 is a photodetector that receives radiation 150A and converts it into an electronic signal 155. Detector 154 connects to a central computer 156 to process electronic signal 155. Similarly, detector 153 is a photodetector configured for detecting component 150B, which is filtered by vapor filter 152 as filtered component 157. Detector 153 converts component 157 to an electronic signal 158 for processing by central computer 156.

Accordingly, electronic signal 158 corresponds to backscattered laser radiation 148 as filtered by vapor filter 152; and electronic signal 155 corresponds to unfiltered backscattered laser radiation 150A. Electronic signal 155 is thus used to nullify certain anomalies as computer 156 processes electronic signal 158. For example, when processed with electronic signal 158, signal 155 may be used to remove, from signal 158, certain laser transmission power fluctuations in filtered component 157 caused by atmospheric changes in air 144. Such a process is explained in more detail in connection with FIGS. 4-7.

Computer 156 includes lookup tables 170 and 172 that may be utilized to determine temperature and/or pressure as discussed below.

Reference component 143B of the laser radiation 142 is split into two components 159 and 160 by beam splitter 145. Component 160 is directed by beam splitter 145 to vapor filter 152 via mirrored surface 161, to measure filter characteristics, whereas component 159 is directed by beam splitter 145 to detector 162, to generate electronic signal 163. Electronic signal 163 is for example used to normalize power fluctuations in the return of backscattered laser radiation 148 caused by power fluctuations in the generation of laser radiation 142 by laser 141. Such a process is explained in more detail in FIGS. 4-7.

Vapor filter 152 filters component 160 to produce filtered component 164. Filtered component 164 is directed to detector 165, via mirrored surface 166, and then converted to an electronic signal 167. Central computer 156 processes electronic signal 167 to determine filter characteristics, such as frequencies and suppression features of the band stop region of vapor filter 152. One such process is also explained in more detail in context of FIGS. 4-7.

While FIG. 2 shows OADS 140 as having free space optical transmission and optical components such as beam splitters 143, 145 and 151 and mirrors 161 and 166, optical fiber may be used for laser 141 transmission along paths 142, 143A, 143B, 159, 160, 164, 150, 150A, 150B and/or 157; in such an embodiment, fiber splitters may be used in place of beam splitters 143, 151 and 145, and mirrors 161 and/or 166 may be eliminated.

It will also be appreciated that although the embodiment shown in OADS 140 of FIG. 2 employs vapor filter 152, other types of filters may be utilized. For example, notch or optical notch filters such as interference filters, dichroic filters, fiber Bragg grating filters, volume holographic gratings, and/or Rugate filters may be utilized. A filter used in place of vapor filter 152 may advantageously have properties such as: (1) high optical absorption within a stop-band region on the order of 40-60 dB or more; (2) a notch filter absorption width between about 5 GHz and 100 GHz, with an absorption width under 10 GHz being preferred; and (3) steep absorption sidewalls, with a 10%-90% absorption transition occurring within about 5 GHz or less. Pass-band filters may also be used. Single filters with multiple absorption features may be utilized or optical or fiber splitters may be used to route optical signals through multiple filters, each filter having a single absorption feature.

Filters other than atomic vapor filters may provide certain advantages. For example, while the absorption frequencies of atomic vapor filters are reliably tied to properties of an atomic vapor used, their use may constrain an OADS to include a tunable laser having output at such frequencies. However, certain tunable lasers may have improved performance and/or stability at frequencies that do not conveniently match atomic vapor filter absorption frequencies. In particular, Bragg grating filters are a low cost, optical notch filter effective for airspeed measurement at longer wavelengths such as 1550 nm. Certain filters such as interference filters, dichroic filters, fiber Bragg grating filters, volume holographic grating filters, and/or Rugate filters may be designed to have absorption features tuned to a preferred frequency output range of a tunable laser, rather than tuning the laser to the filter. The use of a tunable laser, and a matching notch filter in an OADS may thus (1) enable use of higher laser output power for improved return signal strength, (2) make the OADS more robust with respect to thermal stability, vibration and shock, (3) eliminate hazardous materials (e.g., mercury) from the OADS, and/or (4) reduce size, weight and/or cost of the OADS.

Figure 3:
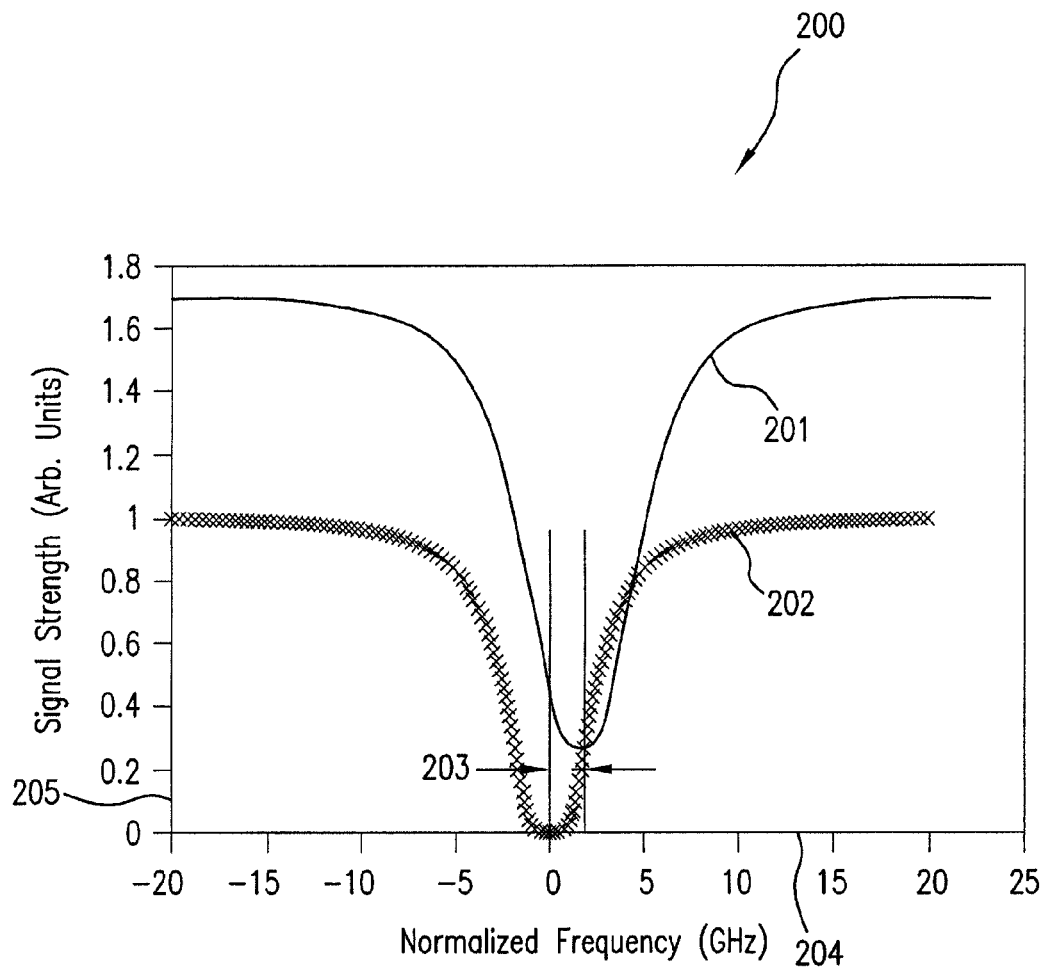
FIG. 3 illustrates an exemplary air speed calculation with an OADS, according to an embodiment.

FIG. 3 shows one graph 200 useful in illustrating an exemplary air speed calculation with OADS 140. Graph 200 shows two curves, 201 and 202, comparing normalized laser radiation magnitudes as a function of frequency (signal strength, that is, normalized laser radiation magnitude, is plotted with respect to axis 205, and frequency is plotted with respect to axis 204). Curve 202 exemplifies filtered radiated laser radiation such as that of filtered component 164 of FIG. 2. As such, curve 202 shows filter characteristics of vapor filter 152 of FIG. 2 determined by processing of electronic signal 167. Curve 202 shows peak absorption of filter 152 occurring at a down-translated frequency of 0 GHz. By way of example, the actual peak absorption frequency of filter 152 may be about 1182.5 THz (i.e., having a corresponding wavelength of about 253.7 nm).

Laser radiation 142 generated by laser 141 passes through filter 152 to provide filtered component 164. Once filtered component 164 is converted to electronic signal 167 by detector 165, computer 156 analyzes and stores features of vapor filter 152 through digital signal processing of signal 167 (e.g., computer 156 stores reference features, obtained under controlled conditions, for use in future calculations). As shown in this example, features of vapor filter 152 have approximately 10% normalized absorption at approximately +/−5 GHz (i.e., 0.9 normalized transmission factor at approximately +/−5 GHz according to axis 205) about the peak absorption frequency. Other types of suitable filters may include different absorption/transmission features.

Curve 201 exemplifies filtered backscattered laser radiation such as that of filtered component 157 of FIG. 2. In one embodiment, curve 201 is used to determine air speed by comparison to curve 202. For example, curve 202 illustrates how vapor filter 152 affects laser radiation 142; curve 201 similarly illustrates how vapor filter 152 affects laser radiation 142 as laser radiation 142 is backscattered (e.g., returns as radiation 148) from air 144. Frequency shift 203 represents the change in frequency of peak absorption for vapor filter 152 between transmitted laser radiation 142 and returned laser radiation 148. Computer 156 processes algorithms applying Doppler velocity equation to determine air speed from frequency shift 203.

To determine air speed in one embodiment, computer 156 determines how far in frequency the peak absorption frequency of filtered component 157 has shifted from the initial laser frequency by comparing curve 202 to curve 201 (e.g., comparing peak absorption frequencies of filtered components 157 and 164). Frequency shift 203 substantially equates to a radial wind velocity through the Doppler velocity equation:

$$\Delta v_D = \frac{2V_R}{\lambda}, \quad (\text{Eq. 1})$$

where $\Delta v_D$ represents the Doppler frequency shift, $V_R$ represents velocity component of the vehicle (e.g., aircraft 101 of FIG. 1) along the laser direction of propagation 143A and $\lambda$ represents the wavelength of laser radiation 142.

In one embodiment, wind velocity component $V_R$ may be measured by determining the frequency shift from curve 202 of graph 200 as compared to curve 201 of graph 200. This is accomplished by calculating a symmetry point of each curve 201 and 202 and determining a difference in symmetry points between the two curves.

Vapor filter 152 may have a plurality of absorption features. Consequently, OADS may have a plurality of absorption maxima, such as those illustrated by curves 201 and 202 of FIG. 3, which may be used to provide a more accurate estimate of the vehicle's velocity. The vehicle's velocity $V_R$ may be calculated using equation 1 for each absorption feature. An average velocity of the vehicle may then be calculated from each value of $V_R$.

FIGS. 4-7 show graphs illustrating exemplary calculations for other air parameters with OADS 140. For example, after determining frequency shift due to air speed as shown in FIG. 3, other air parameters such as air temperature and air pressure may be calculated. In one example, computer 156 initially determines an intensity measurement of the detected backscattered laser radiation (e.g., filtered component 157 detected by detector 153) from electronic signal 158. This experimentally verified intensity measurement of returned laser radiation corresponds to the following equation:

$$S_S(v) = P_L T_L D_S T_R E_S \quad (\text{Eq. 2})$$
$$\int dv_r \int dv_{laser}[L(v_{laser})F(v_r - v)(rR(v_r - (v_{laser} - \Delta v_D)) + mM(v_r - (v_{laser} - \Delta v_D)))]$$

where $S_S(v)$ is electronic signal 158 from detector 153; $P_L$ is the laser power, $T_L$ is the transmission coefficient through air 144 along laser path 143A, $L(v_{laser})$ is the laser line shape inherent to the laser 141 output as a function of laser frequency $v_{laser}$, $T_R$ is the transmission coefficient through air 144 along laser path 148, $E_S$ is optical efficiency of the detector channel through detector 153, $F(v)$ is the band stop frequency range of vapor filter 152 centered at a frequency of $v$, R is Rayleigh scattering as a function of frequency (applicable to the Rayleigh regime) $v_r$ for backscattered laser radiation minus the quantity of laser frequency $v_{laser}$ minus the Doppler shift $\Delta v_D$, r is the Rayleigh scattering magnitude coefficient dependent on air density and the Rayleigh backscattering coefficient, M is Mie scattering as a function of $v_r$ minus the quantity of $v_{laser}$ minus $\Delta v_D$, m is the Mie scattering magnitude coefficient dependent on aerosol concentration and the Mie backscattering coefficient, and $D_S$ is detector 153 efficiency. The Rayleigh backscattering coefficient r and the Mie backscattering coefficient m are constant for a particular atmosphere. These coefficients correspond to the number of scatterers (i.e., molecules for Rayleigh, aerosols for Mie) per unit volume of atmosphere.

Figure 4:
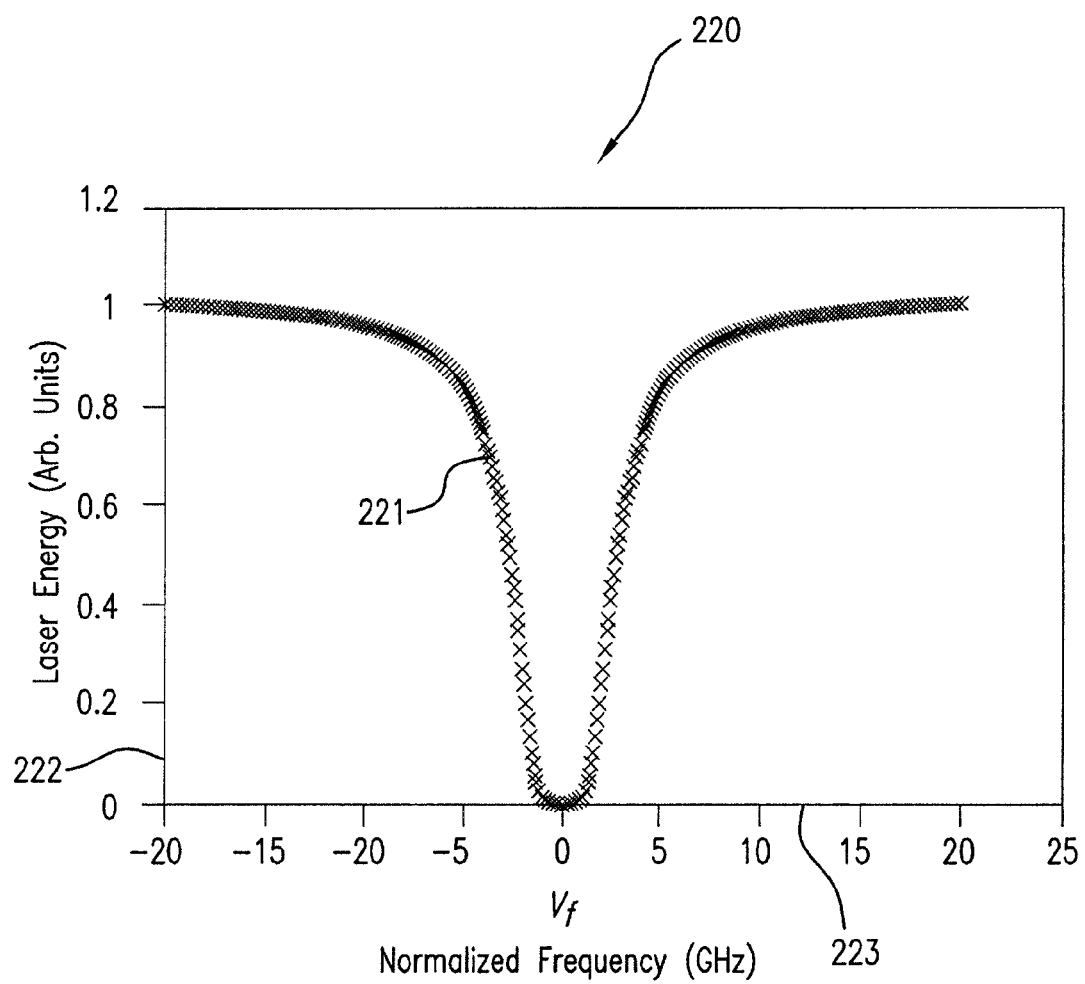
FIGS. 4-7 show graphs illustrating exemplary calculations for other air parameters with an OADS, according to an embodiment.

Next, computer 156 may determine other air parameters, utilizing the result obtained for the measured intensity of the returned laser energy. Such a process, for example, may begin by determining characteristics of vapor filter 152 by transmitting of reference laser radiation 160 through vapor filter 152. For example, measuring band stop characteristics of vapor filter 152 with laser 141 (e.g., via component 143B to electronic signal 167) during experimentation yields a convolution of the laser wavelength and the filter according to the following equation:

$$S_F(v) = P_L E_F D_F \int dv_{laser}[L(v_{laser})F(v_{laser} - v)], \quad (\text{Eq. 3})$$

where $S_F(v)$ is signal 167 from detector 165 as a function of frequency $v$ (e.g., as illustrated in curve 221 of FIG. 4); $E_F$ is the optical efficiency of filter 152 collection along paths 160 and 164, and $D_F$ is detector 165 efficiency.

Note that all optical efficiencies $E_F$ and $E_S$ capture signal losses that are optical in nature. For example, $E_F$, the optical efficiency for detector 165, includes the optical beam splitting ratios for beam splitters 143 and 145, the optical transmission and coupling across filter 152 and the optical delivery efficiency onto detector 165. $E_s$, the optical collection efficiency for detector 153, includes the collection efficiency of telescope 149, the optical coupling efficiency into path 150, the beam splitter ratio of beam splitter 151, the transmission efficiency across filter 152 and the delivery efficiency onto detector 153. Detector efficiencies $D_F$ and $D_S$ include the detector conversion efficiencies for detectors 165 and 153, respectively. Thus, $D_F$ is the conversion efficiency whereby detector 165 converts laser radiation along path 164 into an electrical signal 167. Likewise, $D_S$ is the conversion efficiency whereby detector 153 converts laser radiation along path 157 into an electrical signal 158.

Backscattered laser radiation 148 may include power fluctuations that are caused by laser 141 while generating laser radiation 142. Accordingly, laser radiation detected by detector 162 (e.g., via component 159) may be utilized to normalize power fluctuations attributable to laser 141. In one embodiment, detector 162 converts component 159 into electronic signal 163. In turn, computer 156 processes and normalizes according to the following equation:

$$S_L(v) = P_L E_L D_L \int dv L(v), \quad (\text{Eq. 4})$$

where $S_L(v)$ is the electronic signal 163 from detector 162, $E_L$ is the optical collection efficiency for detector 162, $D_L$ is the conversion efficiency of detector 162 and $P_L$ is the power of laser 141. Note that the optical collection efficiency $E_L$ includes the beam splitting ratios of beam splitters 143 and 145 and the delivery efficiency of laser beam path 159 onto detector 162.

Curve 221 of graph 220 of FIG. 4 represents the magnitude of laser radiation (component 164) filtered by vapor filter 152 and normalized between 0 and 1. Curve 221 represents the magnitude of the laser radiation as a function of frequency (i.e., laser radiation magnitude plotted with respect to axis 222 and frequency plotted with respect to axis 223). Curve 221, therefore, illustrates filtered laser radiation via component 160 as determined by computer processing of electronic signal 167, plotted as laser radiation magnitude normalized between 0 and 1, versus frequency.

In one embodiment, absorption/transmission characteristics of vapor filter 152 are normalized using Eq. 3 and Eq. 4. Eq. 3 yields stop band characteristics of filter 152 and Eq. 4 accounts for power fluctuations in the generation of laser radiation 142. With the power fluctuations of Eq. 4 substantially removed, a "normalization channel" is created, and power fluctuations attributable to atmospheric changes may be accounted for.

In one embodiment, additional power fluctuations caused by atmospheric changes in air 144 are also removed. For example, laser radiation detected by detector 154 (e.g., via component 150A) assists in removing laser power fluctuations caused by atmospheric changes in air 144. Accordingly, detector 154 converts received laser radiation into electronic signal 155. Computer 156, in turn, processes electronic signal 155 to determine the normalized laser radiation magnitude according to the following equation:

$$S_N = P_L T_L T_R E_N D_N \int dv \int dv_{laser}[L(v_{laser})(rR(v-(v_{laser}-\Delta v_D)) + mM(v-(v_{laser}-\Delta v_D)))] \quad \text{(Eq. 5)}$$

where $S_N$ is the signal 155 from detector 154; $E_N$ is optical collection efficiency of the detector 154 and $D_N$ is the conversion efficiency of detector 154.

In one embodiment, it is advantageous to normalize the various characteristic functions to enable a closed-loop solution to the process of determining temperature and pressure. In one example, therefore, computer 156 calculates the normalized laser line shape according to the following equation:

$$\int L(v_{laser}) dv_{laser} = 1, \quad \text{(Eq. 6)}$$

where (as before) $v_{laser}$ is laser line shape frequency and L denotes the laser line shape as a function of frequency. In another example, computer 156 calculates normalized Rayleigh Function according to the following equation:

$$\int R(v_r) dv_r = 1, \quad \text{(Eq. 7)}$$

where R denotes the Rayleigh line shape as a function of frequency $v_r$, applicable to the Rayleigh regime. In another example, computer 156 scales the electronic signal 167 recorded from detector 165 by dividing all recorded values by the maximum value according to the following equation:

$$\text{MAX}(S_F(v)) = 1, \quad \text{(Eq. 8)}$$

where MAX denotes an operation that finds a maximum value of a particular function, and $S_F$ denotes electronic signal 167 measured from detector 165, as a function of frequency $v$ (e.g. as illustrated in curve 221 of FIG. 4). In another example, computer 156 normalizes the Mie Function according to the following equation:

$$M(v) = \delta(v), \quad \text{(Eq. 9)}$$

where $\delta(v)$ is the delta function.

In one embodiment, dividing the signal 167 collected from detector 165 (and represented by Eq. 3, above) by the signal 163 collected from detector 162 (and represented by Eq. 4, above) removes laser 141 power fluctuations, as follows:

$$\frac{S_F(v)}{S_L(v)} = \frac{P_L E_F D_F \int dv_{laser}[L(v_{laser})F(v_{laser}-v)]}{P_L E_L D_L \int dv L(v)} \quad \text{(Eq. 10)}$$

Equation 10 simplifies to:

$$\frac{S_F(v)}{S_L(v)} = \frac{E_F D_F}{E_L D_L} LF(v) \quad \text{(Eq. 11)}$$

where LF(v) represents a convolution of functions L and F (that is, a function that represents the effects of functions L and F combined at each frequency $v$).

In one embodiment, tuning the laser 141 to a reference frequency $v_{ref}$ far enough removed from the effects of the vapor filter 152 enables the measurement of the ratio of the optical and detector efficiencies of the signal channels 167 ($S_F$, represented by Eq. 3 above) and 163 ($S_L$, represented by Eq. 4 above). This, in turn, enables the normalization of the signal 167 measurement to one, for simultaneously checking for laser, detector and filter abnormalities on a scan-by-scan basis:

$$\frac{S_F(v_{ref})}{S_L(v_{ref})} = \frac{E_F D_F}{E_L D_L} \quad \text{(Eq. 12)}$$

In one embodiment, LF(v) are determined to generate a look up table of the convolution of theoretical Rayleigh functions (calculated in terms of temperature and pressure) with the measured filter function. Since the measured filter function is already the convolution of the laser and filter spectra, convolving the Rayleigh function with the measured filter signal 167 yields the expected return signal from an atmosphere of pure Rayleigh scatterers.

In one embodiment, the measured signal 158, which is the backscatter return from the atmosphere 144 that passes through the vapor filter 152 (and is represented by Eq. 2 above), is divided by the signal 155, which is the backscatter return from the atmosphere 144 that does not pass through vapor filter 152 (and is represented by Eq. 5 above). This calculation removes changes in signal transmission that are independent of the factors to be measured:

$$\frac{S_S(v)}{S_N(v)} = \frac{P_L T_L D_S T_R E_S \int dv \int dv_{laser}[(L(v_{laser}) F(v_r-v))(rR(v_r-(v_{laser}-\Delta v_D))+mM(v_r-(v_{laser}-\Delta v_D)))]}{P_L T_L T_R E_N D_N \int dv \int dv_{laser}[L(v_{laser})(rR(v_r-(v_{laser}-\Delta v_D))+mM(v_r-(v_{laser}-\Delta v_D)))]} \quad \text{(Eq. 13)}$$

Since M is a delta function, Equation 13 simplifies to:

$$\frac{S_S(v)}{S_N(v)} = \left[\frac{E_S D_S}{E_N D_N}\right] \frac{rLFR(v_{laser}-\Delta v_D)+mLF(v_{laser}-\Delta v_D)}{r+m} \quad \text{(Eq. 14)}$$

where LFR(v) represents a convolution of functions L, F and R in the sense of the convolution LF(v) discussed above.

In one embodiment, tuning laser 141 to reference frequency $v_{ref}$ far enough removed from the effects of the vapor filter 152 enables the measurement of the ratio of the optical and detector efficiencies of the signal channels 158 ($S_S$ as represented by Eq. 2 above) and 155 ($S_N$ as represented by Eq. 5 above). This enables a check for abnormalities in the filter on a scan-by-scan basis:

$$\frac{S_S(v_{ref})}{S_N(v_{ref})} = \frac{E_S D_S}{E_N D_N} \quad \text{(Eq. 15)}$$

In one embodiment, a variable $K_{ref}$ may be defined as:

$$K_{ref} = \frac{S_S(v_{ref})}{S_N(v_{ref})} \quad \text{(Eq. 16)}$$

Once both data sets (i.e., $S_S$ and $S_N$) are symmetric about the same data point, computer 156 calculates temperature and pressure from the return signal. Initially, computer 156 uses theoretical Rayleigh functions that are functions of temperature and pressure in conjunction with the measured filter transmission to generate a lookup table 170 that stores laser, Rayleigh, and filter (LFR(v)) convolutions that are dependent on atmospheric temperature and pressure. Computer 156 may then compare a normalized return signal to a value stored in lookup table 170 to determine atmospheric temperature and pressure. In order to compare the return signal with the lookup table 170, computer 156 accounts for the magnitude of Mie scatterers as well as any changes in air density that may change the magnitude of the Rayleigh signal.

A vapor filter may be used as a bandstop filter; such filters typically provide frequency stability, optical depth, and optimal filter shape. For the purposes of separating the Rayleigh and Mie scattering, an optical depth of approximately 60 dB provides excellent absorption of Mie scattering within a small frequency variance around $v_0$ (i.e., where $v_f$ is a normalized frequency of 0 GHz). For example, an atomic vapor filter may provide 60 dB of absorption in a frequency region that is not contaminated by Mie scattering. This region may be used in acquiring initial estimates of pressure and temperature (explained below in FIG. 5). Such absorption is observable in FIG. 5 below as the measured signal $S_F$ which has the magnitude of zero centered about $v_0$. This data provides information about pure Rayleigh scattering that may be used to calculate the ratio of Mie scattering to Rayleigh scattering, as shown in Eq. 17:

$$\frac{S_S(v_0)}{S_N(v_0)} = \left[\frac{E_S D_S}{E_N D_N}\right] \frac{rLFR(v_0) + mLF(v_0)}{r + m} \quad \text{(Eq. 17)}$$

Since the vapor filter fully attenuates the Mie scattering in this region:

$$\frac{S_S(v_0)}{S_N(v_0)} = \left[\frac{E_S D_S}{E_N D_N}\right] \frac{rLFR(v_0)}{r + m}, \quad \text{(Eq. 18)}$$

where LFR($v_0$) is the value of the theoretical return signal at particular atmospheric temperature and pressure. Accordingly, computer 156 calculates the ratio of Mie scattering by first defining a variable $K_0$ as follows:

$$K_0 = \frac{S_S(v_0)}{S_N(v_0)} \quad \text{(Eq. 19)}$$

and then solving for the ratio $$\frac{m}{r} = \frac{K_0}{K_a} LFR(v_0) - 1 \quad \text{(Eq. 20)}$$

Using the normalized signal return in the region of interest (i.e., the sloped region between the minimum and maximum of the signal return) and writing the result in terms of the ratio of m over r, yields the following:

$$\frac{S_S(v)}{S_N(v)} = K_a \frac{LFR(v) + \frac{m}{r} LF(v)}{1 + \frac{m}{r}} \quad \text{(Eq. 21)}$$

Substituting the ratio of m and r of Eq. 20 into Eq. 21 yields:

$$\frac{S_S(v)}{S_N(v)} = K_a \frac{LFR(v)}{LFR(v_0)} + LF(v)\left[1 - \frac{K_0}{K_a LFR(v_0)}\right] \quad \text{(Eq. 22)}$$

Solving for LFR(v) yields:

$$LFR(v) = \frac{S_S(v)}{S_N(v)} \frac{LFR(v_0)}{K_a} + LF(v)\left[\frac{1}{K_a} - \frac{LFR(v_0)}{K_0}\right], \quad \text{(Eq. 23)}$$

where the measured signal return LFR(v) is written in terms of measured quantities and the theoretical values of LFR($v_0$)). Computer 156 then calculates LFR(v) and compares it to the lookup table 170 to determine atmospheric temperature and pressure, described in greater detail in FIG. 5.

Accounting for power fluctuations, optical efficiencies and detector efficiencies as described herein allows for an independent check on vapor filter 152 while OADS 140 operates. With variable characteristics of detector channels and power fluctuations accounted for, computer 156 may determine, for example, the substantially constant characteristics of vapor filter 152, such that more accurate measurements of received backscattered laser radiation (e.g., laser radiation 148) are obtained.

In one embodiment, the normalization channel depicted in FIG. 4 is used to remove atmospheric power fluctuations of laser radiation 148. In doing so, computer 156 measures Rayleigh and Mie components of laser radiation 147 in terms of optical efficiencies and detector efficiencies. Such efficiencies are typically measured on a shot-by-shot basis during the analysis process. In an exemplary embodiment of operation, laser 141 generates and transmits laser radiation 142 as a series of pulses at a particular pulse repetition frequency ("PRF"), while in other embodiments laser 141 is a continuous wave laser (as discussed in connection with FIG. 2). Computer 156 then measures the Rayleigh and Mie components in terms of optical efficiencies and detector efficiencies on a pulse-by-pulse basis.

To measure Rayleigh components and Mie components, in one embodiments OADS 140 tunes the frequency of the laser radiation 142 transmitted by laser 141. For example, laser 141 transmits the laser radiation 142 at distal frequencies from the peak absorption frequency of filter 152 (illustrated by $v_f$ in FIG. 4) to provide a frequency-independent measurement. Computer 156 then determines the line shape of laser radiation 142 through filter 152.

In one embodiment, measured intensity of the detected backscattered laser radiation (e.g., as determined by electronic signal 158) is functionally compared to normalized atmospheric factors. The measured intensity often depends upon Mie scatterers (e.g., aerosols) and air density changes due to altitude changes and temperature changes. The air density changes and the temperature changes are not, however, removed through the normalization processes described herein. For computer 156 to accurately determine air parameters such as temperature and pressure of air 144, air density changes are removed from the detected backscattered laser radiation so that computer 156 may accurately determine the air parameters.

Figure 5:
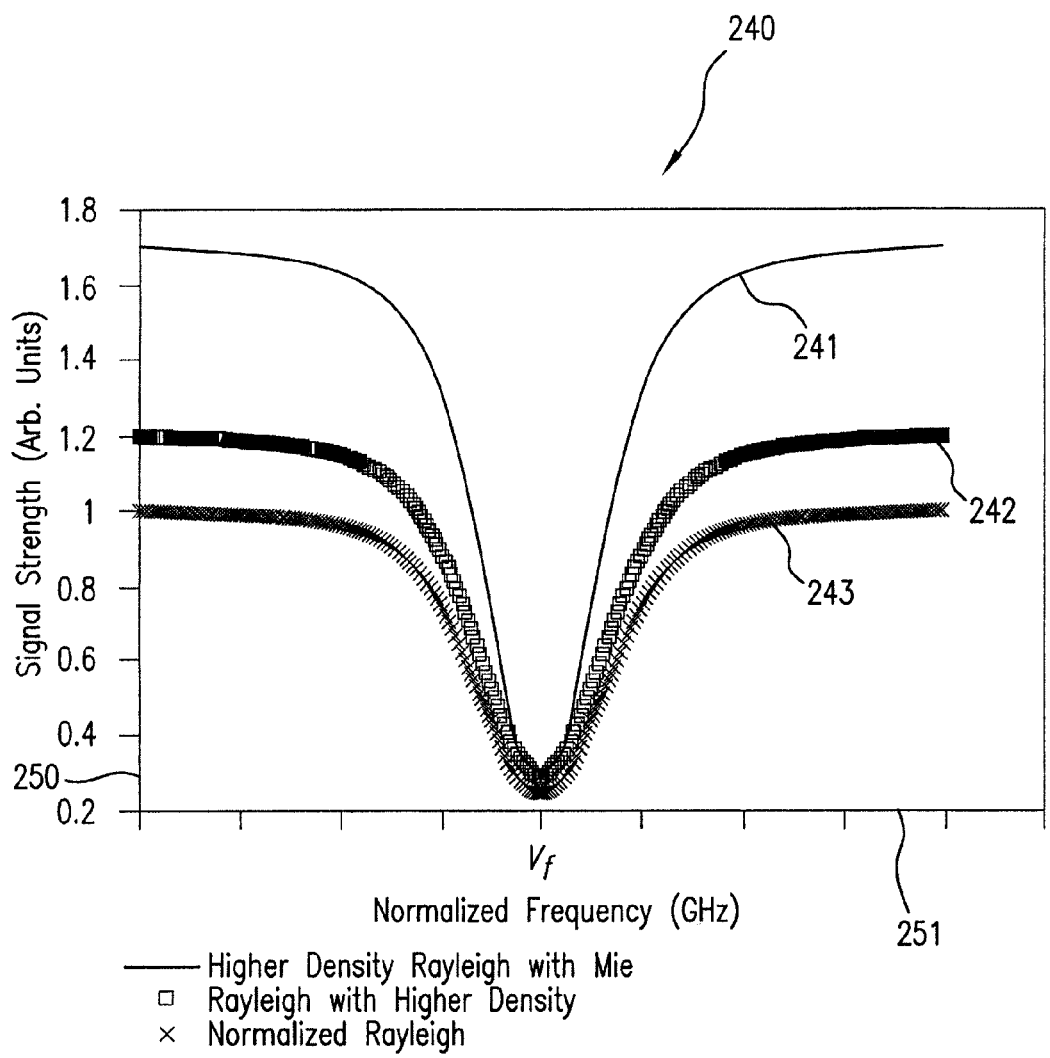

FIG. 5 shows graph 240 with curves 241 (detected backscattered laser radiation at a higher air density causing both Rayleigh and Mie scattering), 242 (detected backscattered laser radiation at an air density causing Rayleigh scattering) and 243 (normalized Rayleigh scattering). Curves 241, 242 and 243 illustrate laser radiation magnitudes (plotted with respect to axis 250) as a function of frequency (plotted with respect to axis 251). In one embodiment, computer 156 processes data from curves 241, 242 and 243 to determine other air parameters. For example, Mie scattering effects are substantially isolated and removed from calculations to determine air temperature and air pressure, since these Mie scattering effects produce inaccurate measurements due to inconsistent aerosol concentrations.

In one embodiment, to determine the air temperature and air pressure, computer 156 processes the data from curves 241, 242 and 243 to substantially isolate and remove the Mie scattering effects, such as those found in curve 241. In processing the data from curves 241, 242 and 243, computer 156 calculates lookup table 170 in substantially real time using a measured laser/filter profile (i.e., as measured at detector 165 of FIG. 2) convolved with theoretical Rayleigh functions for a particular temperature and pressure (e.g., illustrated by curves 242 and 243). Computer 156 then scales the measured return signal LFR(v) (i.e., illustrated by curve 241 in this example) with the ratio of m to r determined by Eq. 20. Computer 156 then analyzes data near the deepest portion of the filter attenuation (i.e., approximately +/−0.5 GHz from $v_f$) to estimate pressure and/or temperature. This portion corresponds to a 60 dB region of absorption that is not contaminated by Mie scattering. Use of this region is a preferred aspect of the calculation technique that provides temperature and pressure accuracy by providing a reliable temperature base from which to increment temperature and/or pressure estimates.

Computer 156 calculates theoretical Rayleigh return assuming an initial temperature estimate and performs a Least Square Error (LSE) calculation to determine the accuracy of the temperature with respect to the theoretical Rayleigh function. Computer 156 repeats the process with incremental changes to temperature and/or pressure until an optimal fit (i.e., an LSE calculation that corresponds to design specifications) is achieved. Although discussed in detail with respect to LSE, other approximation methods, such as Newton-Raphson and Monte Carlo, may be used in alternative embodiments. Accordingly, this disclosure teaches by way of example and not by limitation.

Temperature affects air density in a manner that is reciprocal to pressure; increasing pressure increases density, while increasing temperature decreases density. Additionally, increasing temperature increases the Rayleigh lineshape width while increasing pressure increases the Rayleigh lineshape height. Accordingly, for each incremental value of temperature and/or pressure, the Rayleigh lineshape is unique. Such scattering theory is discussed in "On The Kinetic Model Description Of Rayleigh-Brillouin Scattering From Molecular Gases", G. C. Tenti, D. Boley and R. C. Desai, Canadian Journal of Physics, vol. 52, pg. 285-290 (1974).

In one example, computer 156 determines air density changes by aligning peak absorption frequencies of curves 241, 242 and 243, illustrated at frequency $v_f$. Since curve 243 represents detected backscattered laser radiation containing substantially no Mie scattering, curve 243 may be used as a reference where Mie scattering has been eliminated. In one example, computer 156, therefore, uses curve 243 to remove the effects of Mie scattering by aligning curves 241, 242 and 243 and by calculating a ratio of the detected backscattered laser radiation to theoretically pure Rayleigh scattering (the ratio of curves 241 and 242) which may be utilized to determine air density. Mie scattering effects are then removed by subtracting curve 243 from the calculated ratio of curves 241 and 242. With Mie scattering essentially removed from the measurement, computer 156 more accurately determines air temperatures and air pressures.

Figure 6:
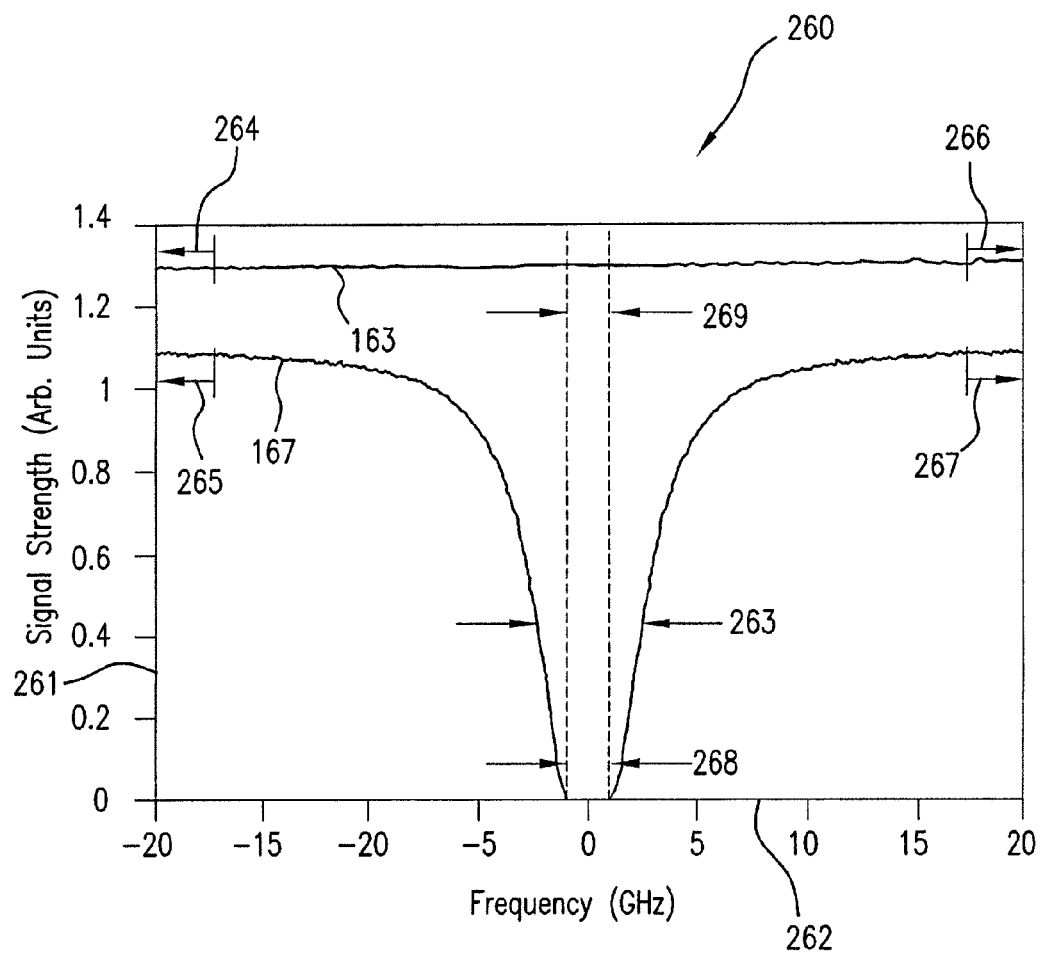
Figure 7:
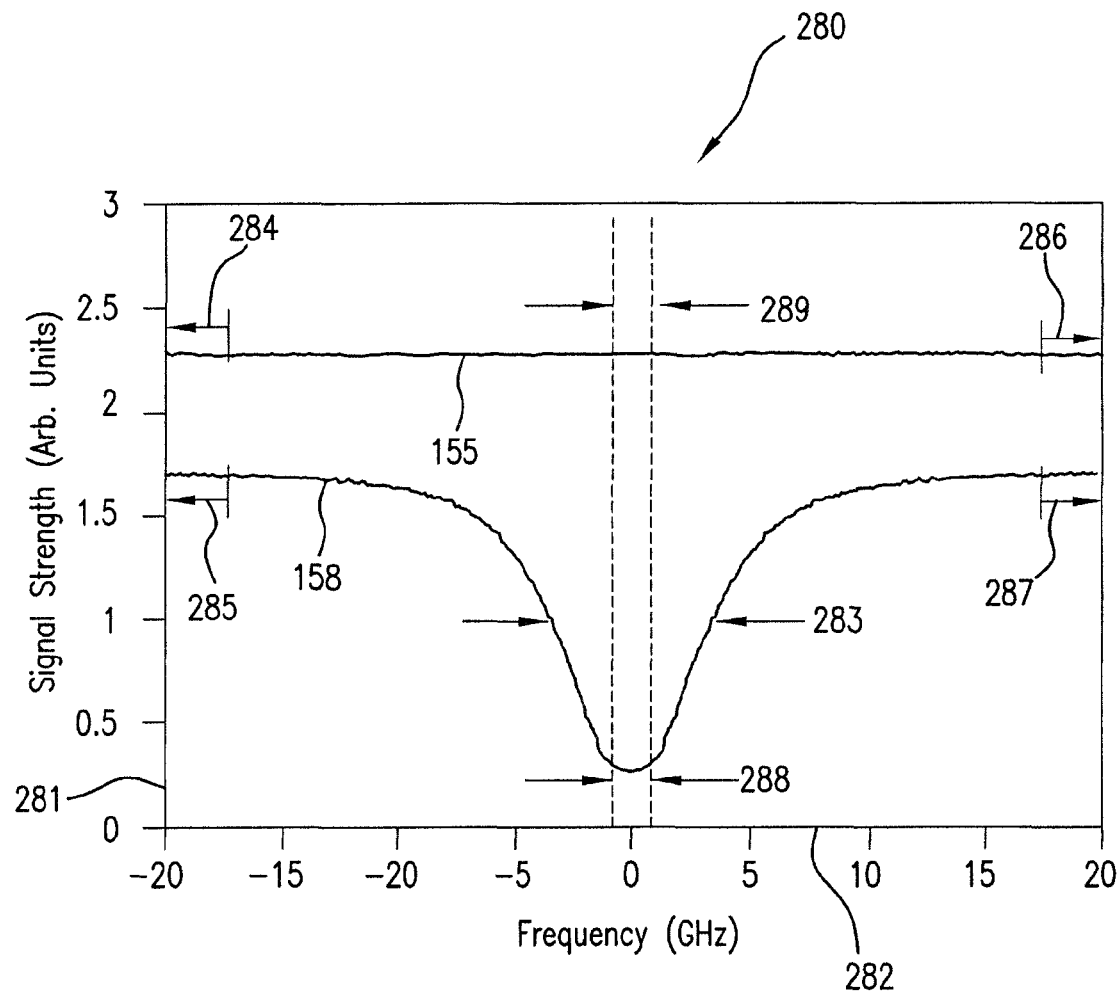

FIGS. 6 and 7 show other exemplary graphs that may be used in determining air pressure and air temperature. FIG. 6 illustrates a graph 260 of electronic signals 163 and 167 of FIG. 2 respectively generated by detectors 162 and 165 of FIG. 2. Graph 260 shows electronic signals 163 and 167, that represent light intensity as a function of normalized signal strength (axis 261), versus frequency (axis 262). FIG. 7 illustrates a graph 280 of electronic signals 158 and 155 (see FIG. 2) generated by detectors 153 and 154 respectively, representing light intensity as a function of normalized signal strength (axis 281), versus frequency (axis 282). These four light intensities (represented by electronic signals 163, 167, 158 and 155) may be measured, over time, through transmission and collection of light corresponding to laser pulses, or they may be measured through transmission and collection of light corresponding to a continuous wave laser whose frequency varies continuously. In one example, a transmission frequency of laser radiation 142 of FIG. 2 generated by laser 141 at a certain PRF may sweep such that each laser pulse is emitted at a different frequency. Electronic signals 163 and 167 therefore illustrate how laser radiation 142 of laser 141 may sweep in frequency across an absorption band 263 of the vapor filter 152. Illustratively, FIG. 6 shows one complete frequency sweep of laser radiation 142 generated by laser 141 and detected by detectors 162 and 165. Similarly, electronic signals 155 and 158 of FIG. 7 show detected signals of detectors 153 and 154 as laser radiation 142 of laser 141 performs a complete sweep in frequency across absorption band 283 of vapor filter 152.

From signals 163 and 167, computer 156 may for example determine a normalized filter transmission, by dividing discrete points of electronic signal 167 by corresponding discrete points of signal 163. Similarly, computer 156 may determine a normalized atmospheric return though vapor filter 152 by dividing discrete points of signal 158 by corresponding discrete points of signal 155. These discrete points, described herein, correspond to individual pulses of laser radiation 142.

Using normalized calculations of filter transmission (e.g., from graph 260) and the normalized calculations of atmospheric return (e.g., from graph 280), computer 156 determines relative optical efficiencies in the vapor filter 152.

In one embodiment, computer 156 determines optical transmission for vapor filter 152 using the frequency independent components of data from graph 260, FIG. 6 (there is substantially no change in amplitude for signals 163 and 167 at frequencies greater in magnitude than ±18 GHz from 0 GHz illustrated at points 264, 265, 266 and 267). Computer 156 therefore determines a ratio of optical transmission for vapor filter 152 by calculating a ratio of signal 167 to signal 163, via frequency corresponding points of the signals, for points representing frequencies greater in magnitude than ±18 GHz from 0 GHz.

Similarly, computer 156 determines a magnitude of intensity of atmospheric-returned laser radiation received through vapor filter 152 using the frequency independent parts of the data from graph 280, FIG. 7 (there is substantially no change in amplitude for signals 155 and 158 at frequencies greater in magnitude than ±18 GHz from 0 GHz illustrated at points 284, 285, 286 and 287). Computer 156 thereby determines a ratio of atmospheric return with the laser power measurement by calculating a ratio of signal 158 to signal 155 via frequency corresponding points of the signals for points representing the frequencies greater in magnitude than ±18 GHz from 0 GHz.

In one embodiment, computer 156 calculates a ratio of signal 158 to signal 155 for frequencies between ±0.5 GHz (illustrated at points 288 and 289). Such a frequency range includes substantially no Mie scattering of laser radiation 142 for air 144; it thus corresponds to substantially pure Rayleigh scattering. Computer 156 thus compares a Rayleigh to Mie scattering strength based upon the ratio of signal 158 to signal 155. Computer 156 determines Rayleigh to Mie scattering strength by comparing a ratio of signal 158 to signal 155 at frequencies between ±0.5 GHz to the ratio of signal 158 to signal 155 at frequencies greater than ±18 GHz from 0 GHz. In one embodiment, computer 156 performs similar calculations for "non-scattered" laser radiation 142 (e.g., component 143B of FIG. 2) based on data illustrated in FIG. 6 using points 268 and 269. Such a process is further described in FIG. 8.

Ratios determined for the non-scattered laser radiation 142 and for the scattered laser radiation 148 may be used in tandem to numerically calculate Laser-Rayleigh-Filter convolution (e.g., LRF(v)) from data. The Laser-Rayleigh-Filter convolution is in turn compared to a look up table of theoretical Laser-Rayleigh-Filter convolution values to determine temperature and pressure.

Figure 8:
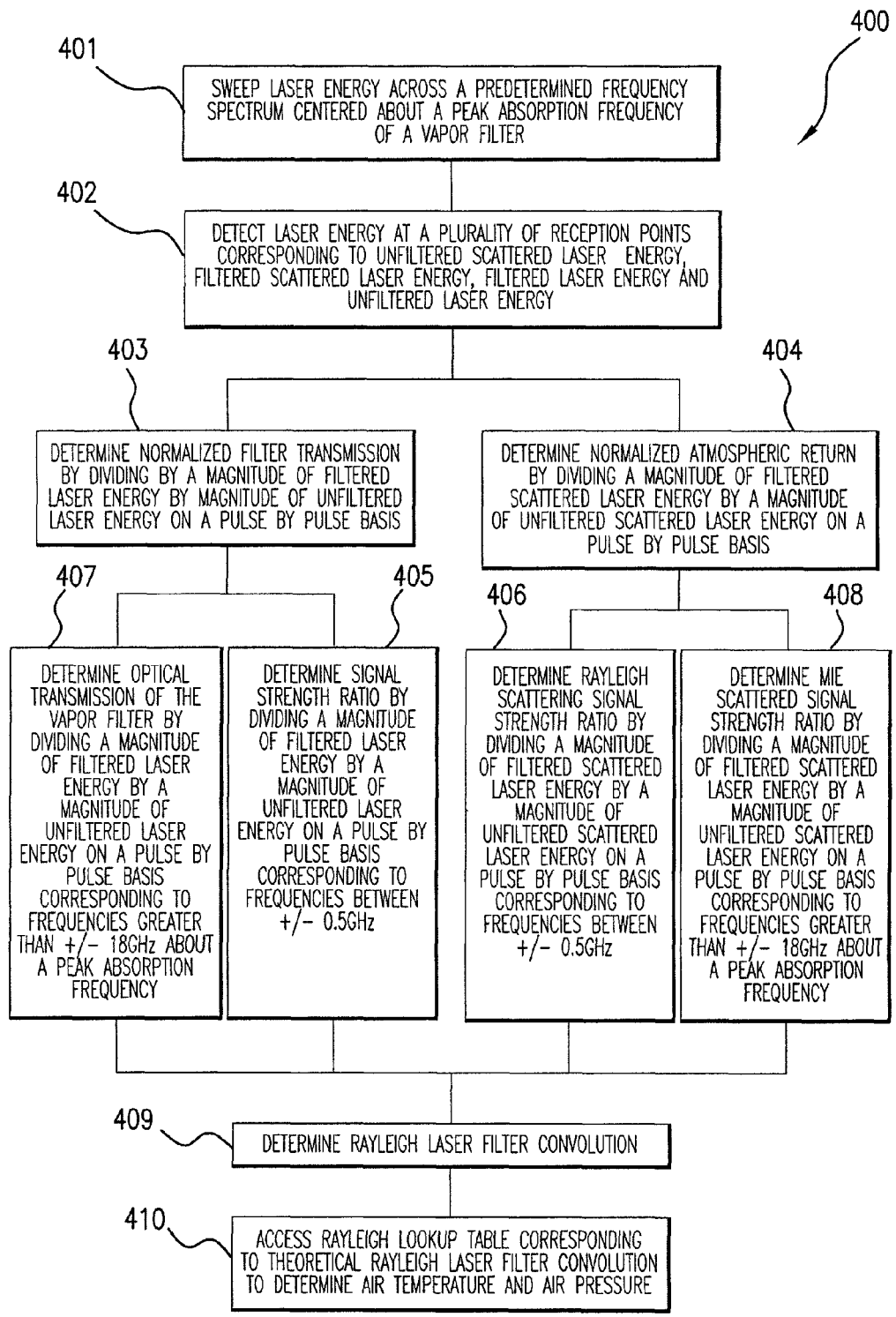
FIG. 8 is a flowchart showing one exemplary method of operation of an OADS, according to an embodiment.

FIG. 8 shows a flowchart of one exemplary methodical operation 400 of an OADS. Method 400 may be partially or fully performed by computer 156 of OADS 140; computer 156 may receive operating instructions from software and/or firmware. A laser (e.g., laser 141 of FIG. 2) sweeps laser radiation across a predetermined frequency spectrum, in step 401. The laser may sweep the laser radiation across a frequency range of about +/−20 GHz by transmitting laser radiation at a certain PRF (or it may sweep frequency continuously, as discussed in connection with FIG. 2 above). In one embodiment, the PRF is about 1 kHz, with a pulse width between about 50 ns and 100 ns, and a swept frequency range is centered about a frequency corresponding to a peak absorption frequency (e.g., 260 nm) of a filter (e.g., vapor filter 152, FIG. 2).

Laser radiation is typically split into four distinct paths such that the laser radiation may be detected as four different inputs, in step 402. These four paths of laser radiation correspond to: 1) laser radiation transmitted by the laser (e.g., component 159 of FIG. 2); 2) laser radiation transmitted by the laser through the filter (e.g., component 164 of FIG. 2); 3) laser radiation transmitted by the laser into the air and backscattered (e.g., component 150A of FIG. 2); and 4) laser radiation transmitted by the laser into the air and backscattered through the filter (e.g., component 157 of FIG. 2). For simplicity, these components are hereinafter referred to as: 1) unfiltered laser radiation; 2) filtered laser radiation; 3) unfiltered backscattered laser radiation or unfiltered scattered laser radiation; and 4) filtered backscattered laser radiation or filtered scattered laser radiation.

After detecting the four components of laser radiation, a computer (e.g., computer 156, FIG. 2), determines normalized filter transmission of the vapor filter, in step 403. For example, the computer, in one embodiment, processes the unfiltered laser radiation and filtered laser radiation by dividing the magnitude of the filtered laser radiation by the magnitude of the unfiltered laser radiation. In one embodiment, the division is performed on a pulse-by-pulse basis, where divided magnitudes of the pulses have corresponding frequencies.

The computer also determines, in one embodiment, a normalized atmospheric return of the laser radiation, in step 404. For example, the computer may process the filtered backscattered laser radiation and unfiltered backscattered laser radiation by dividing the magnitude of the filtered backscattered laser radiation by the magnitude of the unfiltered backscattered laser radiation. Again, in one embodiment, division is performed on a pulse-by-pulse basis, where divided magnitudes of the pulses have corresponding frequencies.

Once normalized filter transmission and normalized atmospheric return of the laser radiation are determined, the computer determines signal strengths for each of the filter transmission and the atmospheric return. For example, the computer determines the optical transmission through the filter by calculating a ratio of the filtered laser radiation to the unfiltered laser radiation at particular frequency ranges, in steps 405 and 407. The computer similarly determines the atmospheric return (scattering) signal strength through the filter by calculating a ratio of the filtered backscattered laser radiation to the unfiltered laser radiation at particular frequency ranges, in steps 406 and 408.

The computer also determines a signal strength ratio for the normalized filter transmission by dividing filtered laser radiation by unfiltered laser radiation, again on a pulse-by-pulse basis, at frequencies greater in magnitude than about +/−18 GHz about the peak absorption frequency, in step 407. The computer further determines a signal strength ratio for the normalized filter transmission by dividing filtered laser radiation by unfiltered laser radiation on a pulse-by-pulse basis at frequencies between about +/−0.5 GHz, in step 405. These signal strength determinations correspond to frequency ranges where Mie scattering (e.g., +/−18 GHz) and Rayleigh scattering (e.g., +/−0.5 GHz) are most prevalent, and are thus useful when combined with similar signal strength determinations for the normalized atmospheric return. The computer determines a Mie scattering signal strength ratio for the normalized atmospheric return of the laser radiation by dividing filtered backscattered laser radiation by unfiltered backscattered laser radiation, again on a pulse by pulse basis, at frequencies greater in magnitude than about +/−18 GHz about the peak absorption frequency, in step 408. The computer also determines a Rayleigh scattering signal strength ratio for the normalized atmospheric return of the laser radiation by dividing filtered scattered laser radiation by unfiltered backscattered laser radiation on a pulse-by-pulse basis at frequencies between about +/−0.5 GHz in step 406.

With signal optical transmission for the filter and signal strengths for both Rayleigh scattering and Mie scattering determined, the computer determines a Rayleigh laser filter convolution in step 409. For example, the computer, in one embodiment, performs a convolution of the optical transmission with the Rayleigh and Mie scattering signal strengths corresponding to the frequency ranges for Rayleigh and Mie scattering of +/−0.5 GHz and +/−18 GHz, respectively. The computer then accesses a lookup table, such as lookup table 170 of FIG. 2, that has theoretical Rayleigh laser filter convolution values to determine temperature and pressure of the air, in step 410.

It is also possible to calculate a convolution of a measured filter function with a theoretical Rayleigh-Brillouin return (Rayleigh line shape), and directly compare the convolution with filtered scattered laser radiation. This allows calculation of atmospheric parameters without calculating a deconvolution of the Rayleigh-Brillouin signal, reducing the complexity of real-time calculations required to determine the atmospheric parameters. In particular, ratios of measured signals may be compared directly to theoretical ratios of a Rayleigh line shape convolved with measured filter functions to allow self calibrating measurements. For example, signal strength variations across data gathering channels and power of scattered laser radiation may be inherently normalized when such ratios are used. Certain ratios of measured data at laser frequencies that lie within filtered bands of optical notch filters (e.g., absorption features of an atomic vapor cell, or equivalent features of other filters, as discussed above) may be useful for determining temperature and pressure, since Mie scattering is eliminated firm the measured data. Calculation of convolutions may represent a lower computational burden on a computer (e.g., computer 156 of OADS 140) as compared to calculating deconvolutions of measured data into and out of a Rayleigh-Brillouin representation.

For example, filtered scattered laser radiation data in a signal channel may be characterized by the equation:

$$S_S(v) = P_L T_L T_R E_S D_S \int\int dv_1 dv_r L(v_{laser}) F(v_1 - v) \quad \text{(Eq. 24)}$$
$$(rR(v - (v_r - \Delta v_D)) + mM(v - (v_r - \Delta v_D)))$$

where parameters are as previously defined, and a subscript 1 indicates a measurement frequency 1. Eq. 24 may be simplified by using the notation $LFR(v)$ for the convolution of laser, filter function and Rayleigh return, as defined above, and a similar notation $LFM(v)$ for a convolution of laser, filter function, and Mie scattering return:

$$S_S(v_1) = P_{L1} T_{L1} T_{R1} E_{S1} D_{S1} [rLFR(v_1) + mLFM(v_1)] \quad \text{(Eq. 25)}$$

If frequency 1 is located in a filter absorption band, the Mie scattering term is effectively eliminated, yielding:

$$S_S(v_1) = P_{L1} T_{L1} T_{R1} E_{S1} D_{S1} rLFR(v_1) \quad \text{(Eq. 26)}$$

Forming a ratio of a signal obtained at frequency 1 with a signal obtained at another frequency 2 in another filter absorption band yields:

$$\frac{S_S(v_1)}{S_S(v_2)} = \left[\frac{P_{La}L_{La}T_{Ra}E_{Sa}D_{Sa}}{P_{Lb}L_{Lb}T_{Rb}E_{Sb}D_{Sb}}\right]\left[\frac{r_a(r_b + m_b)}{r_b(r_a + m_a)}\right]\left[\frac{LFR(v_1)}{LFR(v_2)}\right] \quad \text{(Eq. 27)}$$

where frequency 1 is measured at time a and frequency 2 is measured at time b. If times a and b are close enough to each other that no atmospheric changes occur between time a and time b (or if measurements are interspersed in such a way that average values of parameters such as P, L, T, E, D and r are identical over a time span of the measurements) then the ratio of Eq. 27 simplifies further to:

$$\frac{S_S(v_1)}{S_S(v_2)} = \frac{LFR(v_1)}{LFR(v_2)} \quad \text{(Eq. 28)}$$

In one embodiment, a lookup table stores temperature and pressure pairs that correspond with two of the measurement ratios defined in Eq. 28. The two ratios essentially define two equations with two unknowns (i.e., a single such ratio may not determine both pressure and temperature). Data may also be taken in more than three filtered bands, yielding more than two of the Eq. 28 ratios; when more than two such ratios are available, multiple values of temperature and pressure may be determined that may be averaged or used in "best fit" methods to improve temperature and pressure determination in a noisy measurement environment.

In an embodiment, theoretical Rayleigh line shapes corresponding to temperature and pressure combinations are stored in a lookup table. A reference curve is calculated by obtaining a Rayleigh line shape corresponding to an estimated temperature and pressure from the lookup table and convolving the Rayleigh line shape with a normalized atmospheric return curve. Values of $LFR(v)$ at absorption feature maxima may then be determined from the reference curve and used to determine one or more air parameters (e.g. temperature and/or pressure) using Eq. 28.

Calculating convolution of the measured filter function with the theoretical Rayleigh line shape also enables utilization of curve fitting routines to map the convolved curves to true temperature and pressure conditions, such that the deconvolution calculations suggested by the Tenti, Boley and Desai paper above are not required. An OADS may store a precompiled table of stored curve shapes that are generated by modeling large databases of known temperature and pressure values (e.g., the table may be stored in computer 156 of OADS 140). As measurements are taken, data curves may be generated from measured data, and curve-fitting routines may be used to compare the data curves to the stored curve shapes to derive true temperature and pressure. The utilization of curve-fitting routines may also have less sensitivity to noisy data, as compared to deconvolution calculations, making the determination of true temperature and pressure more robust.

Figure 9:
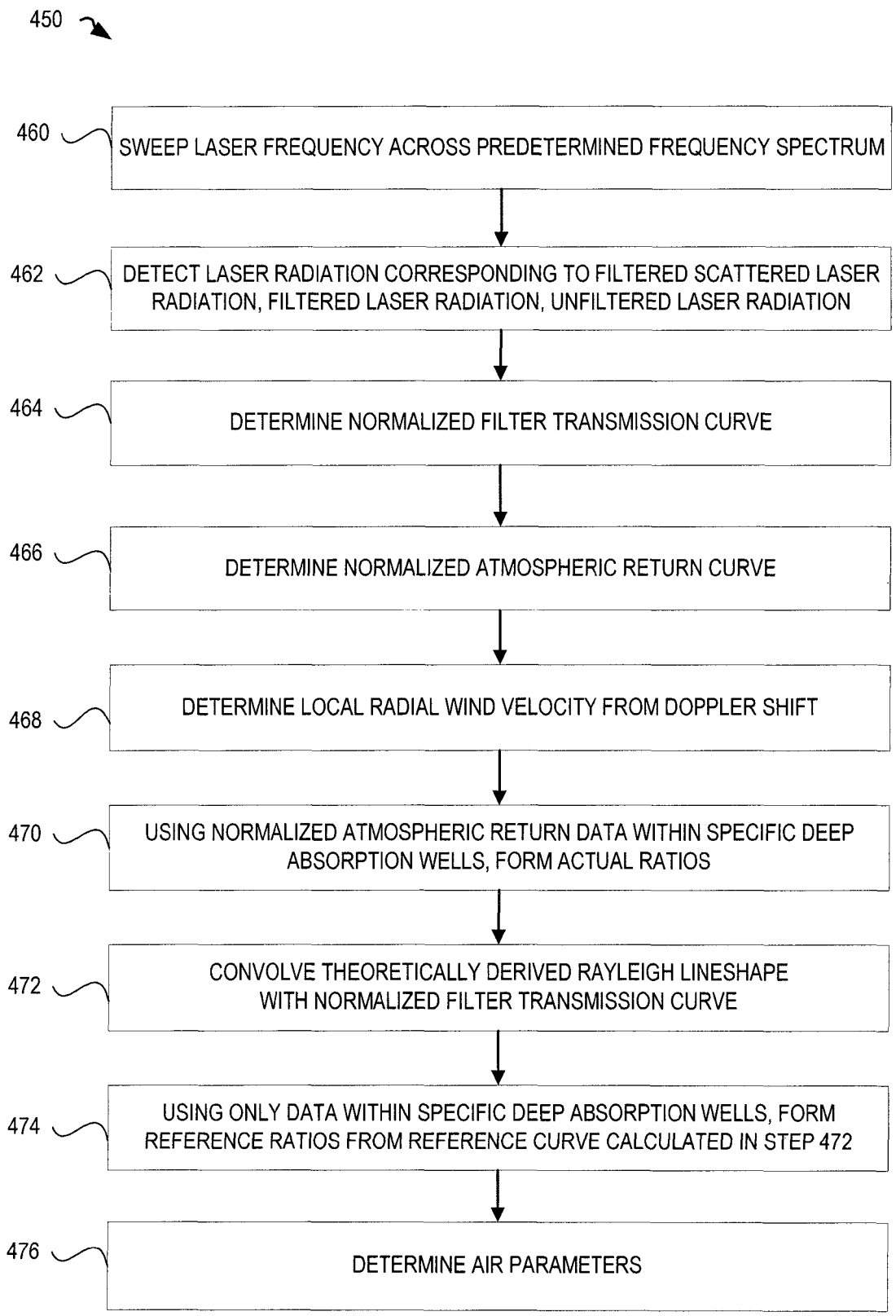
FIG. 9 is a flowchart showing one exemplary method of operation of an OADS, according to an embodiment.

FIG. 9 is a flowchart showing one exemplary method of operation 450 of an OADS, which may be used to calculate one or more air parameters. Method 450 may be partially or fully performed by computer 156 of OADS 140; computer 156 may receive operating instructions from software and/or firmware.

In an embodiment of step 460, a laser (e.g., laser 141 of FIG. 2) sweeps laser radiation across a predetermined frequency range (swept frequency range) that is centered about a deep absorption line of a filter. The laser may sweep the laser radiation across a swept frequency range of about +/−20 GHz by transmitting the laser radiation at a certain PRF, or by sweeping the frequency of a continuous wave laser. In one embodiment, a PRF is about 1 kHz, with a pulse width between about 50 ns and 100 ns, and the swept frequency range is centered about a frequency corresponding to a peak absorption frequency (e.g., 260 nm) of a filter (e.g., vapor filter 152, FIG. 2, or an interference filter, a fiber Bragg grating filter, a dichroic filter, a volume holographic grating filter, or a Rugate filter). In an embodiment, the swept frequency range includes frequencies corresponding to at least two absorption features of at least one band stop filter. In another embodiment, the swept frequency range includes frequencies corresponding to at least three absorption features of at least one band stop filter.

Step 462 detects laser radiation corresponding to filtered scattered laser radiation (e.g. component 157 of FIG. 2), filtered laser radiation (e.g. component 164 of FIG. 2), and unfiltered laser radiation (e.g. component 159 of FIG. 2) at each frequency; each step 460 and 462 is for example performed for each laser pulse in the swept frequency range.

Step 464 determines a normalized filter transmission curve by dividing a magnitude of filtered laser radiation by a magnitude of unfiltered laser radiation for each pulse in the swept frequency range; step 466 determines a normalized atmospheric return curve by dividing a magnitude of filtered scattered laser radiation by a magnitude of unfiltered laser radiation for each pulse in the swept frequency range. It will be appreciated that since the data required for the calculations in steps 464 and 466 are collected by the operation of steps 460 and 462, steps 464 and 466 may be done in any order or in parallel.

Step 468 calculates a Doppler shift $\Delta v_D$ that is a frequency shift between the normalized filter transmission curve (calculated in step 464) and the normalized atmospheric return curve (calculated in step 466), then calculates a local radial wind velocity $v_R$ using Eq. 1 above. As was stated above, a band stop filter may have a plurality of absorption features; consequently, a plurality of Doppler shift $\Delta v_D$ and radial wind velocity $v_R$ calculations may be calculated in step 468.

Step 470 utilizes only normalized atmospheric return curve magnitude values (calculated in step 466) within three or more specific filter absorption bands to form two or more normalized atmospheric return ratios (actual ratios). For example, if atmospheric return data is derived for frequencies 1, 2, and 3 (at times that are close enough together, as discussed with reference to Eq. 28 above), then two ratios may be formed using one of the frequencies as a baseline (denominator), such as $$\frac{S_S(v_1)}{S_S(v_2)} \text{ and } \frac{S_S(v_3)}{S_S(v_2)}.$$

Atmospheric return curve magnitude values corresponding to absorption feature maxima of one or more band stop filters may be used. One atmospheric return ratio (actual ratio) may be determined if for example only one air parameter (e.g. pressure or temperature) is to be calculated.

Step 472 obtains theoretical temperature and pressure data from a lookup table of normalized filter transmission convolved with theoretically derived Rayleigh line shapes, at the frequencies utilized in step 470. One or more air parameters (e.g. temperature and/or pressure) are then estimated. A Rayleigh line shape corresponding to the estimated one or more air parameters is for example obtained from a lookup table. A reference curve is then calculated by convolving the Rayleigh line shape with the normalized filter transmission curve from step 464.

In step 474, ratios corresponding to the ratios formed in step 470 are formed from magnitude values of the reference curve calculated in step 472. The ratios formed in step 474 may be referred to as reference ratios.

In step 476, one or more air parameters (e.g. temperature and pressure) are determined. An error corresponding to the differences between the one or more actual ratios and the corresponding one or more reference ratios may be calculated: if the error is within an acceptable range, the estimated one or more air parameters (corresponding to the Rayleigh line shape) are published as the actual one or more air parameters; but if the error is not within an acceptable range, steps 472, 474, and 476 are repeated with one or more different estimated air parameters until the error is within an acceptable range.

The error of step 476 may be calculated using a least mean square error algorithm. Steps 470, 474, and 476 may be optional; the normalized atmospheric return curve calculated in step 466 is for example correlated to the reference curve calculated in step 472 using curve fitting routines.

Certain advantages of embodiments described above may include:
(1) Obtaining accurate computations of various air parameters, such as air speed, air temperature and air pressure, substantially regardless of altitude and/or Mie scattering;
(2) Obtaining a system that accurately performs in a variety of vibrational environments;
(3) Obtaining an ability to determine temperature and pressure within a particular region of atmosphere without a prior knowledge of the atmosphere;
(4) Reducing need for on-aircraft system calibrations and system health checks, as compared to existing systems;
(5) Providing robustness with respect to high vibration environments;
(6) Obtaining faster calculations and/or reduced computational requirements placed on aircraft computers, as compared to existing systems;
(7) Ability to accurately calculate velocity in environments with changing temperature and/or pressure; and/or
(8) Ability to accurately calculate one or more air parameters (e.g. velocity, temperature, and/or pressure) without precise control of laser frequency.

It can be desirable to measure air parameters, such as velocity and temperature, at selected distances (or ranges) from an Outside Air Data System. In an aircraft, discrepancies between air velocity near the aircraft and air velocity in a more distant zone ahead of the aircraft can provide warning of wind shear or microburst activity. In ground-based applications, it is known that wind speed, wind direction, and air temperature can vary with altitude, and altitude above an air data system corresponds to range above the system.

An OADS of the type discussed herein with reference to FIGS. 1-9 can be operated in a pulsed mode. In this mode, each time laser 141 emits a pulse of laser radiation, measurements are taken by detector 153 at one or more of several specific time delays following the pulse. Air data parameters derived from measurements made at each specific time delay from the pulse correspond to air data parameters at a particular distance or range from the OADS system.

An alternative embodiment of the OADS that provides for range resolution and permits use of lower cost lasers by allowing the OADS to operate at a lower peak laser output power is the "Random Modulated Continuous Wave"

Figure 10:
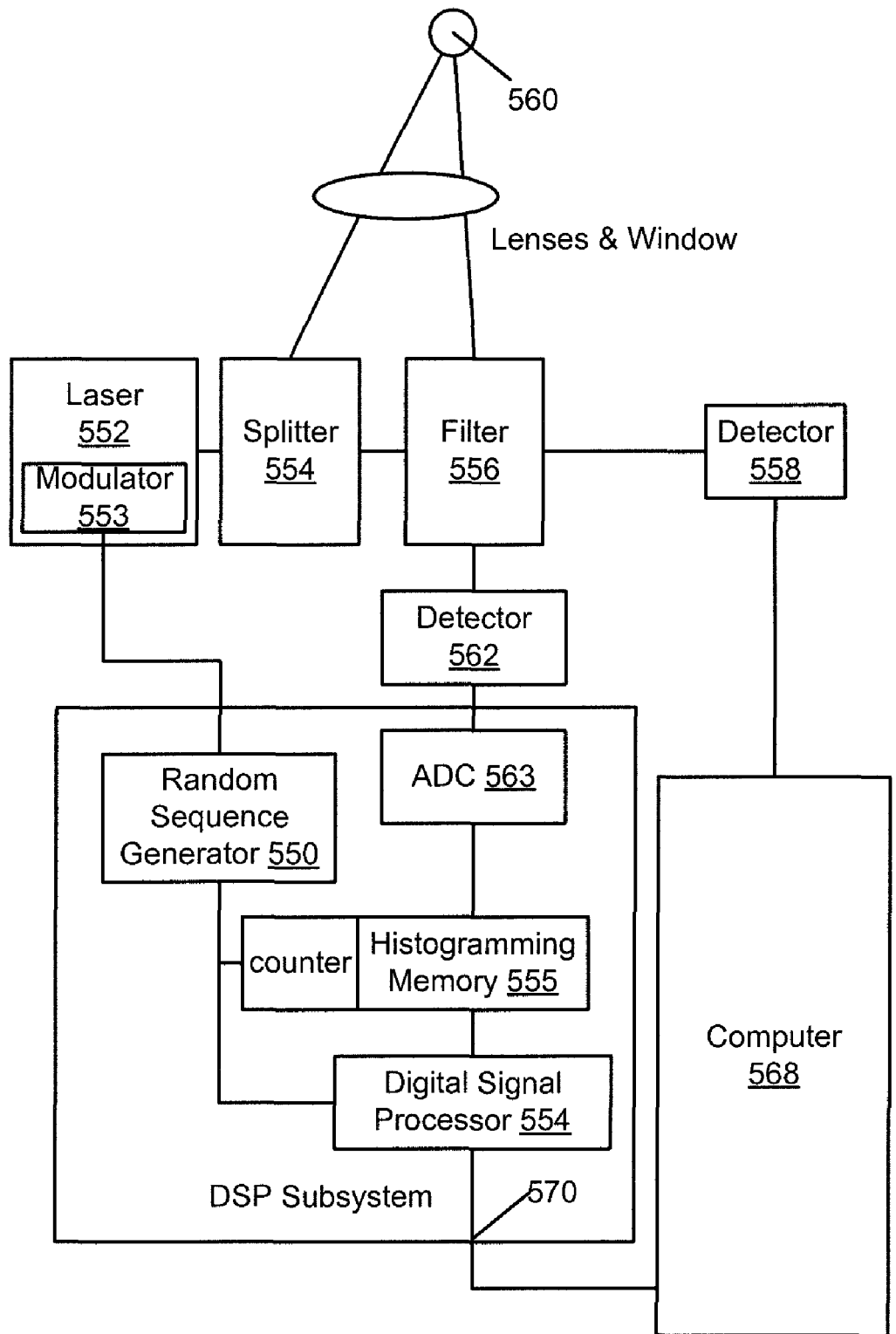
FIG. 10 is a block diagram of an embodiment of the OADS using the Random Modulated Continuous Wave approach to range resolution.

(RMCW) approach illustrated in FIG. 10. In this system, a pseudorandom sequence generator 550 generates continuously, and repeatedly, a binary pseudorandom code sequence. The pseudorandom code possesses a delta-function autocorrelation, meaning that a mathematical cross-correlation of the code with itself produces a delta function at zero time delay. The pseudorandom code is sent to an amplitude modulator 553, which amplitude modulates a tunable laser 552; tunable laser 552 corresponds to laser 141 of FIG. 2. Modulator 553 may be an integral subsection of the laser 552, such is the case with diode lasers, or may be a separate component exterior to laser 552, such as Lithium:Niobate modulators, acousto-optic modulators or similar devices. Laser radiation from laser 552 enters a beam splitter 554. A portion of radiation from beam splitter 554 passes through filter 556 and reaches detector 558. Another portion of radiation from beam splitter 554 is transmitted into the air, is scattered by, and subjected to Doppler shift by, aerosol and molecular scatterers 560, and returned to the OADS where it passes through filter 556 to detector 562.

Meanwhile, the pseudorandom code from sequence generator 550 is passed to a digital signal processor 554 to be used in interpreting the output from detector 562. The output from detector 562 is first converted to a digital representation using the analog-to-digital converter 563. For each of the pseudorandom code generated by sequence generator 550, the output from the analog-to-digital converter 563 is added into a unique memory location. These "n" unique memory locations are collectively termed a Histogramming Memory 555. Likewise, the Histogramming Memory 555 returns to the first unique memory location and begins summing each new output from the analog-to-digital converter 563 to accumulated value contained in each unique memory location, starting with the first unique location and proceeding in sequence. This continuous process is repeated once, or as many times as desired.

One embodiment repeatedly transmits and collects sufficient iterations through the pseudorandom sequence into the Histogramming Memory 555 until a sufficient lidar Signal-to-Noise Ratio (or similar lidar system performance metric) is achieved. Once sufficient data is collected in the Histogramming Memory 555, the "n" values accumulated into the "n" unique memory locations are passed to the digital signal processor 554. The digital signal processor 554 performs a mathematical cross-correlation on the two "n" valued sequences: one arriving from the pseudorandom code generator 550 and one arriving from the Histogramming Memory 555. The resultant output is termed the correlated signal 570 and provides the range-resolved return signal. The correlated signal 570 is then used to determine air parameters at all specific distances from the OADS.

Figure 11:
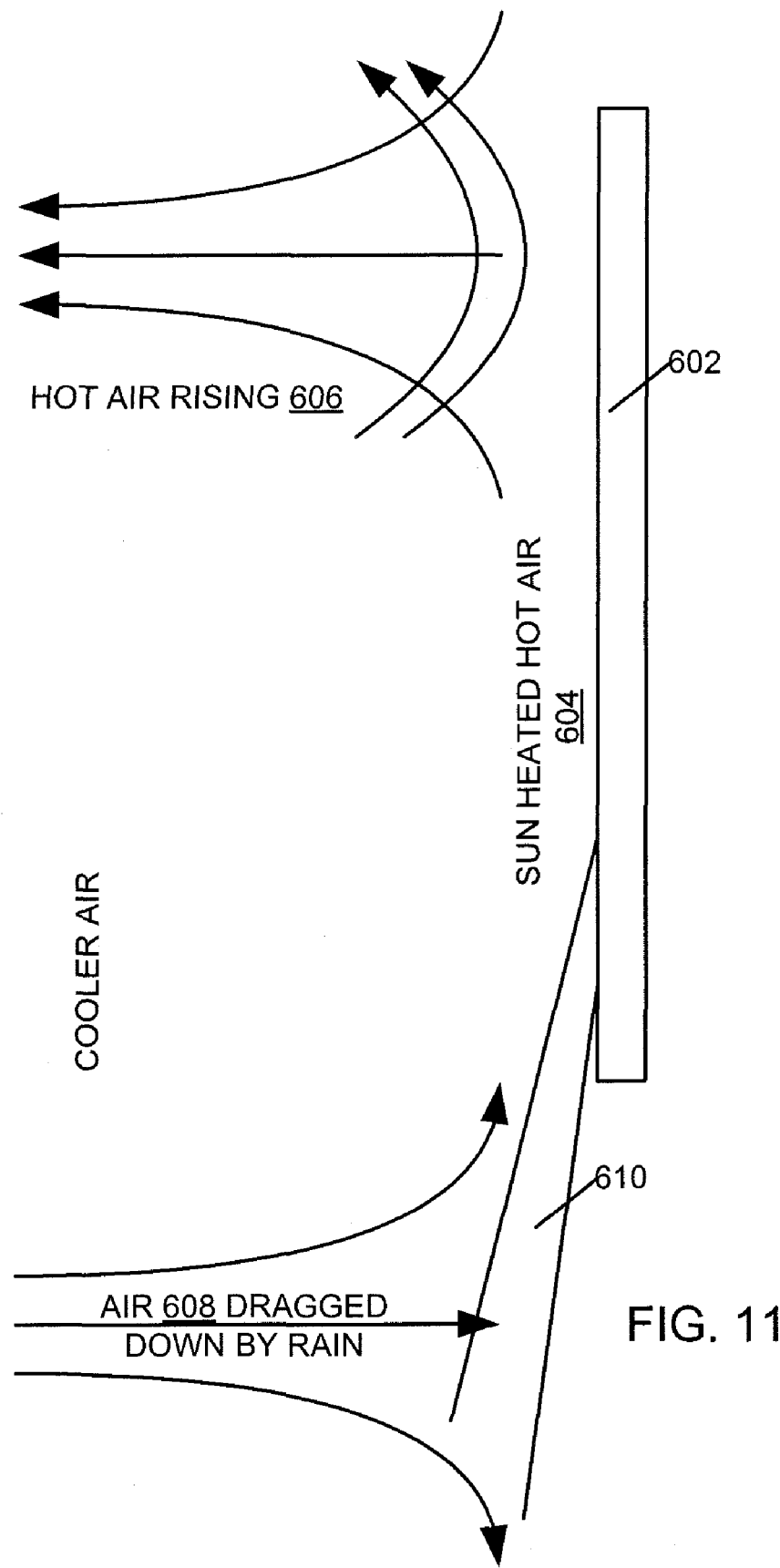
FIG. 11 illustrates some wind conditions that can cause hazard to aircraft near airports or to wind power systems.

During hot summer days in large parts of the United States, air 604 is heated near the surface, as for example a runway 602 (FIG. 11). By afternoon, this often results in "unstable air" conditions, where warm air 604 may rise 606, sometimes rapidly. Air is drawn inward towards the base of the resultant rising column of air, and may begin to rotate. Depending on conditions, the resultant disturbance may range from a "dust-devil" to trigger more widespread phenomena like a thunderstorm, hurricane, or tornado. Even a dust-devil can pose hazard to an aircraft that attempts to land or takeoff through it. Similarly, dust-devils can cause sharp wind gusts that can pose problems for wind power systems they may encounter.

Rising hot air may carry moisture with it, and may rise to high altitudes where the moisture condenses into rain. Falling rain may drag an air column downwards 608, sometimes quite quickly. Since the ground impedes airflow, air from the downmoving air column 608 may blast outwards in one or more directions from a center of the column in a phenomenon known as a microburst. Aircraft typically land along a glideslope 610 of between three and six degrees from the horizontal, and typically maintain a predetermined approach airspeed along an approach path aligned with the runway while doing so. According to investigators, a Lockheed L-1011 attempted landing at Dallas while a microburst intersected the approach path. As it descended along the glideslope, it first met with headwinds, then a downdraft, and finally a tailwind. The L-1011 slowed to maintain airspeed while in the headwind, and by the time it passed through the downdraft into the tailwind zone it had insufficient airspeed to continue flying—and sank into the ground short of the runway. This accident led to great interest in detecting microbursts and other low-level wind shear near airports so that similar events can be avoided.

Figure 12:
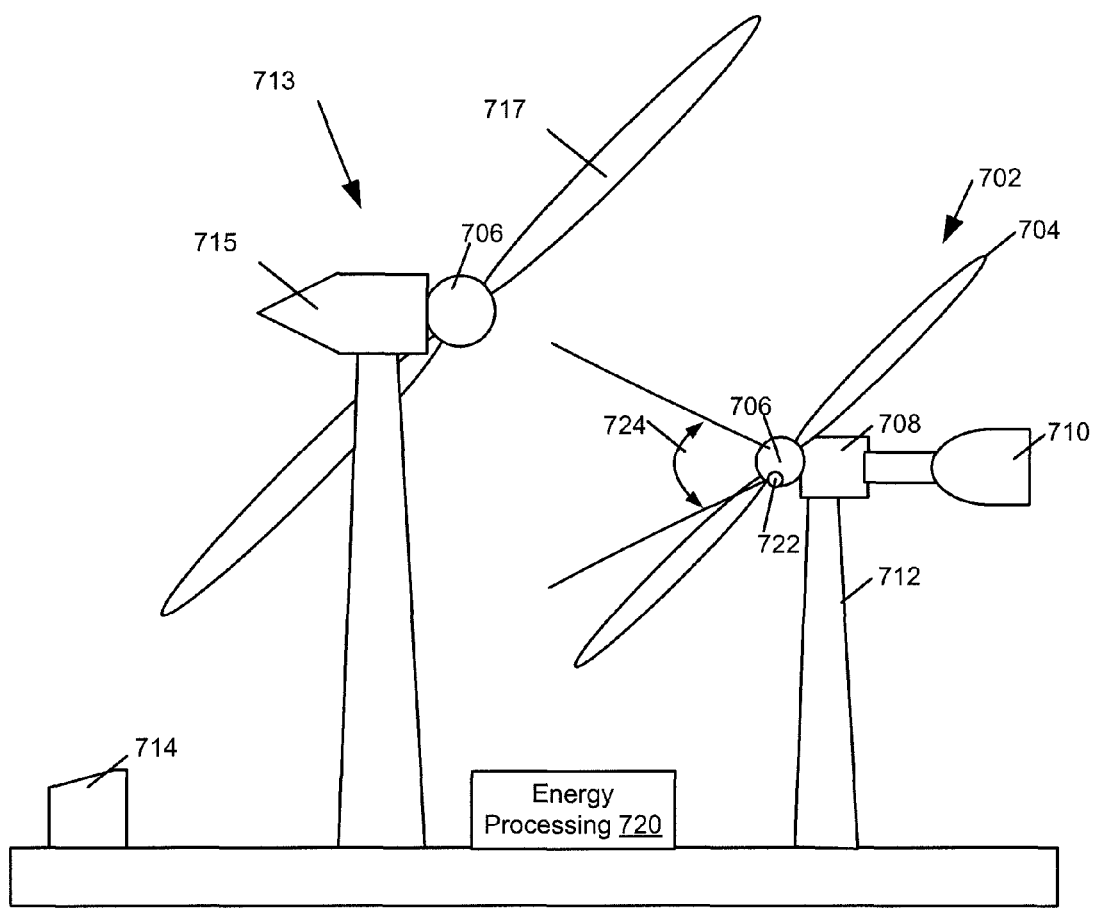
FIG. 12 illustrates application to a wind power system.

Wind power systems, such as illustrated in FIG. 12, produce power in amounts that vary drastically with wind velocity. In particular, no power is generated when wind velocity falls below a minimum, or cut-in, windspeed. This minimum is a function of specific wind turbine parameters including gear ratio between hub and generator, generator design, blade design, and blade length. These wind turbine parameters also partly determine an optimum power generating wind velocity range for the wind turbine.

Wind power systems may also be damaged by high winds or turbulence. Wind turbines typically have maximum allowable wind conditions for operation determined by these wind turbine parameters as well as other wind-turbine specific parameters such as tower height and strength, blade strength, and hub bearing design—when wind velocity or turbulence exceeds this maximum, the wind turbine generally must furl and when furled generates no power. Since wind may vary with season, as well as with terrain, it is desirable to record wind conditions at brief intervals over an extended time—extending over at least several months to a year—to determine suitable locations and optimum wind-turbine specifications for construction of wind power systems or wind farms. It is desirable to obtain wind speed and direction data at multiple altitudes at each proposed site, including at the surface, at hub altitude, and at blade minimum and maximum altitudes; obtaining this data is part of a site survey for a wind power system. The accumulated data may be used to determine optimum wind-turbine specifications for, and predict expected power output of the wind-power system from, a wind power system or wind farm.

Typically, wind power systems have an array of one or more wind turbines 702. Large wind power systems, known as wind farms, may include dozens or even hundreds of individual wind turbines near each other and located in favorable locations having favorable wind, such as the Altamont Pass near Livermore, Calif. Each wind turbine 702 of the system has one, two, or more blades 704 attached to a hub 706 that directly, or indirectly through a transmission, drives a generator that is typically located in a nacelle 708.

Most wind turbines are of the horizontal axis type, and require an orientation subsystem to ensure the wind turbine and its blades are maintained at a proper angle to the wind despite changes in wind direction. The orientation subsystem may take the form of a tail 710 as commonly used with smaller wind turbines having blades upwind of tower 712. In some other wind turbines 713, the orientation system has a pivot (not shown) under the nacelle 715 with blades 717 placed on a downwind side of tower 712 such that wind drag on the blades tends to orient the wind turbine at a correct angle to the wind. The orientation subsystem typically includes a pivotable attachment (not shown) of nacelle 708, 715 to tower 712. Other forms of active and passive orientation systems are known.

Many wind turbines have a furling system which coarsens or feathers blade pitch, or directs the blades away from the wind, to protect the turbine from potentially damaging winds such as wind gusts or high winds and storm conditions; the furling system may interact with the orientation system or with a blade pitch system. Other variations are known including air brakes, mechanical brakes, and retractable mountings.

Many wind turbines have a pitch system for controlling blade pitch, where an angle of attack of blade 704 to wind is varied from a fine pitch in low winds through a coarse pitch in higher winds to a feathered pitch in potentially damaging wind conditions—blade pitch control can serve as a furling system. Some larger wind turbines have independent blade pitch control where the angle of attack of the blades can be adjusted independently, and in some systems blade pitches can be independently adjusted cyclically through a revolution.

Electrical energy is collected from generators of all wind turbines 702 of a system by energy collection and processing apparatus 720; once collected the energy may be fed to the power grid, stored for later use, or used locally.

Wind turbines are available in a wide variety of types and sizes ranging from small turbines of a few watts capacity, such as have been used to provide a small amount of electrical power to a glider or airplane, through turbines of a few hundred or a few thousand watts capacity such as are often used for off-grid residences, to large turbines having over 2 megawatts of peak output capacity and which typically feed a large power grid. Wind systems may include more than one type of wind turbine, and may be supplemented or collocated with other types of renewable and/or non-renewable energy generation apparatus.

Wind turbines 702 and associated towers 712, including blades 704, are subject to variable, and occasionally large, wind loads. Since blades 704 are often quite long, their rapidly rotating mass combined with high and possibly imbalanced wind loads can cause substantial vibration and stress at nacelle and tower. Excess wind loads have caused damage to turbines and towers, up to and including collapse.

Wind shear is a local weather condition where wind velocity and/or direction varies with altitude, this can result from turbulence from hills, trees, other wind turbines, and ridgelines as well as from convective phenomena like microbursts and dust-devils. In addition to wind shear posing a hazard to aircraft near an airport, it also poses a hazard to wind turbines as blades may be exposed to wind forces that vary substantially through a revolution, in turn aggravating vibration and load stress. A standard solution to this problem is to increase tower height so that the wind turbine is exposed to more uniform wind than available at lower altitude—this can greatly increase tower expense and strength requirements and other solutions are desirable. Vibration over extended periods has caused damage to turbines and towers, including metal fatigue of towers. If wind speed and direction versus altitude are known, vibration induced by wind shear can also be reduced by adjusting blade pitch as a blade swings from one altitude to another, such that stress on high blades is more evenly balanced by stress on lower blades.

It is known that thunderstorms, microburst, and dust-devil conditions, as well as other weather conditions, can cause gusty conditions that may result in a wind load on a blade 704 of a wind turbine changing dramatically in a matter of seconds; these conditions can therefore change from good power-generation conditions to conditions requiring altered blade pitch or even rapid furling to avoid excessive wind load and damage to the turbine or tower.

Many wind turbines sense changed wind conditions by monitoring power output and/or rotational rate of blades 704, these wind turbines can only respond alter changes have occurred.

A ground-mounted air data system 714 may be located near one or more wind turbines of a system to provide additional and early real-time wind information, and information regarding unstable air conditions, with which to optimize blade pitch, or to furl, before those conditions reach the wind turbine. Similarly, an air-data system 722 may be located in a hub or nacelle of a wind turbine to provide information on approaching winds—including warning of oncoming gusts.

U.S. Pat. Nos. 7,342,323, 7,281,891, and 6,320,272 describe wind turbines that include laser wind velocity measurement systems mounted on the nacelle or on a hub of a wind turbine, to determine the air velocities in front of the wind turbine. The systems change blade pitch dependent on measured on-coming wind velocities. All of these systems use a coherent, pulsed or continuous wave, lidar. Such systems can only use Mie scattering and cannot utilize Rayleigh scattering, decreasing their measurement robustness in clear atmospheric air and precluding their ability to measure atmospheric temperature or pressure. Such systems measure velocities but assume that wind direction is constant with altitude and aligned with the wind turbine's axis. Some of these systems measure windspeed variation with altitude; the system of U.S. Pat. No. 7,281,891 in particular has an off-axis hub-mounted lidar that scans a conical region ahead of the turbine as the turbine rotates. The system of U.S. Pat. No. 7,281,891 discloses detection of windspeed by Doppler lidar techniques over a conical scanned region, but does not disclose detection of temperature or details of lidar operation and range determination.

We therefore offer a ground-based wind mapping system for site survey and/or system control that is capable of mapping and recording wind direction and velocity, along with air temperature, at a variety of altitudes and ranges of interest to a wind power system, even when the atmosphere is very clean of aerosols. We also offer a hub mounted system capable of mapping wind direction and velocity at a range of altitudes and ranges in a zone upwind of a wind turbine.

Figure 13:
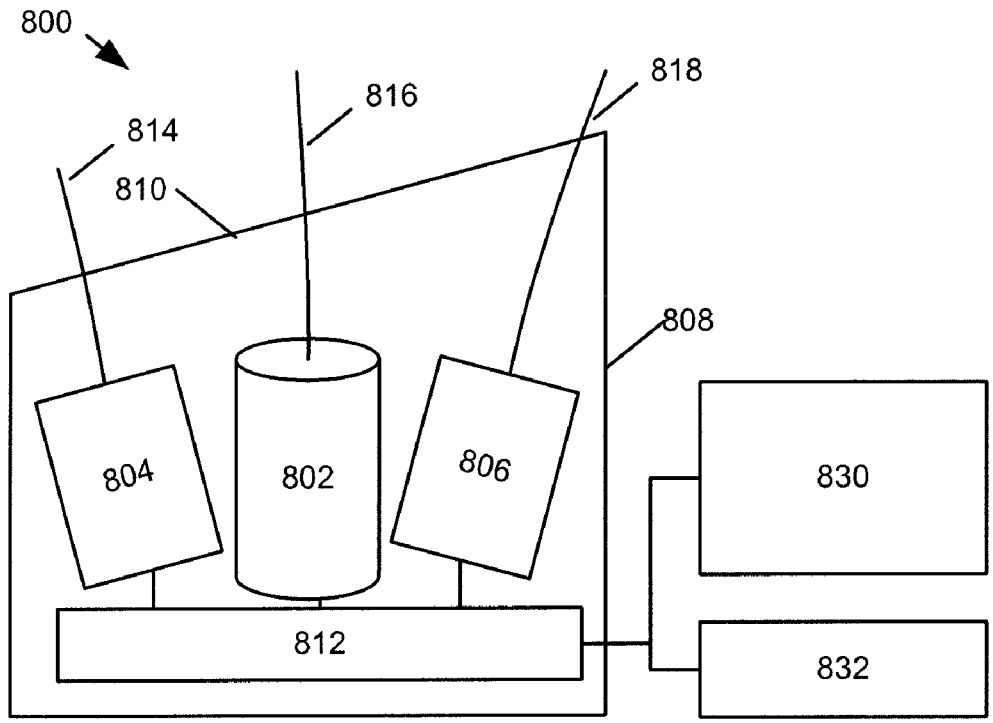
FIG. 13 is a block diagram of an embodiment of an air data system suitable for ground-based applications.

A ground-based air-data system 800 may be assembled as shown in FIG. 13 by assembling three laser transceivers 802, 804, 806 such as the Rayleigh-Mie transceiver device previously described with reference to FIGS. 1-10 into a common housing 808 and a window 810. All three transceivers provide data to, and operate under control of, computer 812. All three transceivers 802, 804, 806 are aimed through the common window 810, however each is aimed along a slightly different axis 814, 816, 818, such that the three axes do not lie in a common plane.

Computer 812 uses each of transceivers 802, 804, 806 to measure a Doppler-shift at a first distance from the system 800. These Doppler-shifts are used, together with a known orientation of the system, by computer 812 to compute a windspeed and direction at that distance or altitude. Similarly, computer 812 uses at least one of transceivers 802, 804, 806, to sense temperature at the same altitude. In an embodiment, windspeed, wind direction, and air temperature are sensed and recorded at several altitudes ranging from zero to two thousand feet, or higher, at periodic time intervals.

The embodiment of FIG. 13 may be combined with a solar power system 830 and digital data recorder 832 to perform site monitoring of a proposed location for wind power systems. In an embodiment the digital data recorder 832 records minimum, average, and peak-gust windspeed with air temperature at four selected altitudes at fifteen minute intervals, and has storage capacity sufficient to do so for at least a month without overwriting recorded data. Other embodiments may record additional data. An anticipated embodiment records minimum, average, and maximum wind speed and direction observations from six altitudes at ten minute intervals. Yet other embodiments of the site survey system may include scanning of an area, as described below with reference to the embodiment of FIG. 15, and recording of windspeed and direction data at multiple altitudes and multiple locations in an area of interest.

The embodiment of FIG. 13 may also be located at an airport to sense wind shear and other wind hazard conditions. Likewise, the embodiment of FIG. 13 may also be used to monitor wind speed and temperature profiles for meteorological applications, including weather monitoring and prediction.

Similarly, embodiments of FIG. 13 may be placed at an airport and aligned along an approach path and glideslope. Since aircraft will be flying towards them, it is necessary that these systems use long wavelengths such as 1500 nanometers that are invisible and non-harmful to the human eye. These devices measure windspeed and direction at several distances along the glideslope; this data can be processed to provide warnings of convective instability, low level wind shear, dust-devil, tornado, hazardous crosswinds, microbursts and similar wind-related hazardous conditions.

In an alternative embodiment of the ground-based air-data system 900, as illustrated in FIG. 14, a transmitter assembly 902 is adapted to provide pseudorandom modulation from modulator 903 to three (or more) incoherent RMCW transmitter laser-telescope transmitter assemblies 904, 906, 908. Each of the three (or more) transmitter laser-telescope assemblies 904, 906, 908 are aligned on a different axis 910, 912, 914, the axes oriented such that the three axes are not mutually coplanar, and aimed through window 916 in a housing 918. Each of the transmitter laser-telescope assemblies transmits modulated laser radiation into the air along its associated axis, where Mie and Rayleigh scattering will take place. In a particular embodiment, the transmitter laser-telescope assemblies operate at 1550 nanometers.

Similarly, a receiver assembly 920 has three (or more) photodetector-telescope assemblies 922, 924, 926 each aligned on an axis 928, 930, 932. Each of these receiver axes 928, 930, 932 is aligned parallel to, and slightly converging with, a transmitter axis 910, 912, 914. Receiver electronics 940, 942, 944 receives signals from an associated photodetector-telescope assembly 922, 924, 926 and correlates the received signal with modulation as sampled from the modulator 903 to provide distance-resolved measurements of Doppler shift of Mie and Rayleigh-scattered radiation received by the associated photodetector-telescope assembly.

Computer 950 receives information from all three (or more) receiver electronics 940, 942, 944 and calculates windspeed and wind direction at various ranges from the apparatus 900 from the received Rayleigh and Mie-scattering data; updating detected windspeed and wind direction measurements every tenth of a second, or faster, as required.

In a particular embodiment, one of the transceivers 904/926, or an additional laser transceiver 952 as previously described with reference to FIGS. 1-10, is used to determine temperature at various ranges from the unit. This unit therefore can provide a profile of windspeed, direction, and temperature with altitude. These measurements can be compared to limits to provide warning of wind-shear at airports or recorded with a digital recorder to perform site survey for wind power systems. Further, with the aid of a separate ground-level humidity sensor, temperature versus altitude data from the system is processed to provide a measure of convective instability; this measure of convective instability provides an early warning of conditions when convective activity such as dust-devils, microbursts, thunderstorms, and tornadoes are likely to develop even if such wind conditions do not yet exist in the field of view of the system.

Temperature versus altitude measurements may be combined with a humidity measurement from other apparatus to give a measure of instability of air. Since unstable air can lead to and powers convective activity, ranging from simple dust-devils to tornadoes all of which may produce gusty conditions; furling thresholds may be reduced by a wind turbine controller when unstable air conditions exist.

Figure 15:
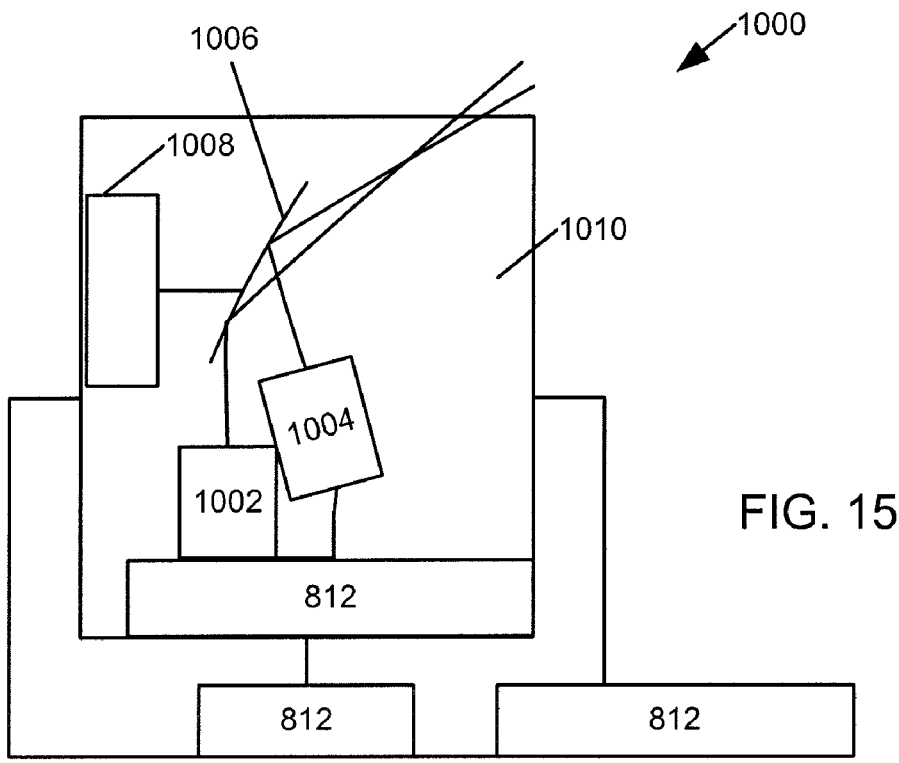
FIG. 15 illustrates a scanning embodiment of the ground-based air data system for mapping windspeed and temperature around a location.

An alternative embodiment of the OADS 1000 is illustrated in FIG. 15. In this embodiment, at least one air data laser transmitter, 1002, and receiver, 1004, as previously discussed with reference to the RMCW OADS of FIGS. 1-10, are aimed at a scanning wedge, 1006, or a holographic grating or steering mirror, for example, that sweeps out an area of interest. The scanning wedge redirects its field of view. The scanning wedge 1006 is attached to a motorized mount 1008 that moves the wedge to scan the field of view of the air data laser transmitter and receiver 1002, 1004 vertically so that field of view is scanned over a range of angles such as angles ranging from the horizon to directly above the OADS.

In an embodiment, the air data laser transmitter 1002, receiver 1004, mirror 1006, and motorized mount 1008 are mounted within a rotatable turret 1010. Rotatable turret 1010 is arranged such that the field of view of the OADS is scanned horizontally over a 360-degree region around the OADS. In an alternative embodiment, the laser transmitter 1002 and receiver 1004 are stationary, but scanning wedge 1006 is rotated by motorized mount 1008 to scan. In this way, the field of view of the OADS is scanned over a hemispherical volume of air centered on the location of the OADS and of radius up to two or more kilometers.

An additional embodiment the OADS resembling that of FIG. 15 includes one air data laser transmitter, 1002, and receiver, 1004, as previously discussed with reference to the RMCW OADS of FIGS. 1-10, is aimed at dual prisms or holographic gratings, (not shown) to direct the scan to any predetermined point in a conical field of view.

An embodiment of the OADS of FIG. 15 has three laser transceivers 1002, 1004 and uses Doppler measurements of all three, with RMCW range discrimination, to determine windspeed and wind direction at various regions of interest in the hemispherical volume of air.

An alternative embodiment of the OADS of FIG. 15 obtains the three Doppler measurements required for wind direction measurements in a region of the hemispherical volume of air from a single laser transmitter 1002 and receiver 1004 by recording Doppler shift measured at two slightly-different vertical angles and two slightly-different horizontal turret or scanning wedge angles. This embodiment is also capable of mapping windspeed and wind direction throughout the hemispherical volume of air.

The OADS of FIG. 15 may be located 714 (FIG. 12) near a wind turbine 702, or near a group of wind turbines, to provide air data at a variety of positions and altitudes for control of the turbines 702. This OADS is capable of detecting wind shear and adverse wind conditions, and adjusting wind turbine 702 by adjusting blade pitch cyclically during turbine rotation, in some embodiments trimming yaw through adjustment of an active orientation subsystem, and furling when necessary, to reduce loads incurred by the blades 704; thereby enabling the wind turbine 702 to better survive. In an embodiment, the wind turbine is therefore better able to survive turbulence and wind shear having differences in wind direction as well as wind speed with altitude and enabled to provide power in conditions that may otherwise require furling. The system therefore provides better protection and utility of wind turbines than systems known in the art. In an embodiment, the computer of the RMCW OADS is programmed to ignore scatter from angles and delays, and hence locations, coincident with locations of wind turbines to avoid reading blade motions as wind.

In another embodiment the RMCW OADS of FIG. 15 may be mounted on the nacelle 708 of a wind turbine and programmed to ignore scatter from angles and delays, and hence locations, coincident with the blades of the wind turbine. In an embodiment, the computer of the RMCW OADS is programmed to ignore scatter from locations of other wind turbines of the wind farm to avoid reading blade motions as wind.

Similarly, the OADS of FIG. 15 may be located near a runway for mapping wind near an airport, or may be positioned at a proposed wind farm site for site survey purposes.

Similarly, the OADS of FIG. 15 may be located in an area, such as a mountain pass, where high, gusty, or turbulent winds may reach levels that pose danger to trucks and other high profile vehicles. The computer of this OADS is programmed to generate traffic alerts when high, gusty, or turbulent winds exceeding a predetermined threshold are detected.

In an alternative embodiment, an RMCW OADS as described with reference to FIGS. 1-10 or FIG. 13 is located 722 in a hub 704 of a wind turbine 702. This OADS is mounted with an axis off-axis with respect to an axis of the wind turbine, such that it maps windspeed and direction at several ranges of a cone 724 ahead of the wind turbine 702. The computer of the RMCW OADS is programmed to ignore scatter from angles and ranges coincident with locations of other wind turbines of the wind farm to prevent reading blade motion as wind.

Since this OADS can sense wind direction, and wind direction variation with range and altitude, as well as wind speed, it detects direction as well as velocity components of wind shear. The OADS therefore provides information for wind turbine 702 to furl or otherwise compensate for such wind shear.

In an alternative embodiment (not illustrated), the OADS is mounted in a blade of a wind power system, and provides both angle-of-attack and relative speed information of wind to blade. This information is used to control blade pitch. The information may also be stored at multiple points during a rotation and used to adjust blade pitch through each rotation of the blade.

Since certain changes may be made in the above methods and systems without departing from the scope of the disclosure herein, it is intended that all matter contained in the above description or shown in the accompanying drawings be interpreted as illustrative and not in a limiting sense. By way of example, those skilled in the art should appreciate that the OADS and the OADS transceivers, as described herein, may be constructed, connected, arranged, and/or combined in ways that are equivalent to what is shown.

What is claimed is:

1. A method for remotely sensing air, comprising:
generating laser radiation with a tunable laser;
splitting the laser radiation into a projected component and a control component;
converting the control component into one or more electronic control signals;
projecting the projected component into the air to induce scattered radiation;
receiving a portion of the scattered radiation as backscattered radiation;
converting the backscattered radiation into one or more electronic backscattered radiation signals, including converting a first portion of the backscattered radiation to an unfiltered backscattered electronic signal, filtering at least a second portion of the backscattered radiation using an optical notch filter to form a filtered portion, and
converting the filtered portion to a filtered backscattered electronic signal;
processing the one or more electronic control signals and the one or more electronic backscattered radiation signals to determine Doppler shift; and
processing the Doppler shift to determine wind speed.

2. The method of claim 1 wherein at least one electronic control signal is derived by filtering the control component with the optical notch filter.

3. The method of claim 2 wherein laser radiation is projected along at least two axes, wherein Doppler shift is determined along each of the axes, and wherein the Doppler shift along each of the axes is used to determine wind speed and direction.

4. The method of claim 3 wherein laser radiation is projected along at least three axes, wherein Doppler shift is determined along each of the axes, and wherein the Doppler shift along each of the axes is used to determine wind speed and direction.

5. The method of claim 4 further comprising scanning the laser radiation to obtain windspeed and wind direction information at multiple locations within a volume of air.

6. The method of claim 4 further comprising periodically recording the windspeed and wind direction for wind power system site survey.

7. The method of claim 4 further comprising modulating the laser with a pseudorandom sequence, storing the received backscatter radiation in a histogramming-type of memory, and correlating this received backscattered radiation with the pseudorandom sequence to obtain windspeed at least one particular distance from the tunable laser.

8. The method of claim 7 further comprising scanning the laser radiation to obtain windspeed and wind direction information at multiple locations within a volume of air.

9. The method of claim 8 further comprising determining blade pitch for at least one blade of a wind turbine.

10. The method of claim 7 further comprising recording the windspeed and wind direction for wind power system site survey.

11. The method of claim 3 further comprising determining air temperature from a Rayleigh-scattered component of the backscattered radiation.

12. The method of claim 2 wherein the laser radiation is emitted into the air from a location on a wind turbine.

13. The method of claim 12 wherein the location on the wind turbine is on a hub or a nacelle of a wind turbine.

14. The method of claim 13 further comprising modulating the laser with a pseudorandom sequence, storing the received backscatter radiation in a histogramming-type of memory, and correlating the received backscattered radiation with the pseudorandom sequence to obtain windspeed at, at least one particular distance from the tunable laser.

15. The method of claim 14 further comprising determining windspeeds and wind directions at a plurality of altitudes, and for determining blade pitch for the wind turbine in response to the windspeeds and wind directions.

16. The method of claim 1 wherein the laser radiation is emitted into the air from a location on a wind turbine.

17. The method of claim 16 wherein the location on the wind turbine is on a hub or a nacelle of a wind turbine.

18. The method of claim 17 further comprising modulating the laser with a pseudorandom sequence, storing the received backscatter radiation in a histogramming-type of memory, and correlating the received backscattered radiation with the pseudorandom sequence to obtain windspeed at, at least one particular distance from the tunable laser.

19. The method of claim 18 further comprising determining windspeeds and wind directions at a plurality of altitudes, and for determining blade pitch for the wind turbine in response to the windspeeds and wind directions.

20. A system for optically sensing air data comprising: a tunable laser for generating laser radiation;
at least one beam splitter for splitting the laser radiation into a projected component and a control component;
at least one optical notch filter;
at least one control component detector coupled to receive at least a portion of the control component through the at least one optical notch filter and generate an electronic control signal therefrom;
apparatus for projecting the projected component into the air to induce scattered radiation and for receiving a portion of the scattered radiation as backscattered radiation;
at least one backscattered radiation detector coupled to receive at least a portion of the backscattered radiation through the at least one optical notch filter and generate an electronic backscatter signal therefrom;
control and computing apparatus for sweeping a wavelength of the tunable laser and for receiving the electronic backscatter signal and the electronic control signal and determining Doppler shift therefrom, and for processing the Doppler shift to determine wind speed.

21. The system of claim 20 further comprising:
a pseudorandom sequence generator for generating a pseudorandom sequence;
a modulator for modulating the laser radiation with the pseudorandom sequence; and
wherein the control and computing apparatus correlates the pseudorandom sequence with the electronic backscatter signal to determine the Doppler shift at a plurality of ranges from the system.

22. The system of claim 21 wherein the control and computing apparatus analyzes the electronic backscatter signal to determine Rayleigh scattering, and to determine air temperature therefrom at a plurality of ranges from the system.

23. The system of claim 22 further comprising a digital data recorder, and wherein the digital data recorder is configurable to record minimum, average, and peak-gust windspeed data with air temperature data at least four times per hour.

24. The system of claim 23 wherein the digital data recorder is configurable to record the minimum, average, and peak-gust windspeeds with air temperature at least four ranges from the system, and wherein the digital data recorder has storage capacity for at least one month of recorded windspeed data.

25. The system of claim 21 wherein the control and computing apparatus analyzes the electronic backscatter signal to determine Rayleigh scattering, and to determine air temperature therefrom at a plurality of ranges from the system.

26. The system of claim 25 wherein the apparatus for projecting the projected component into the air to induce scattered radiation and for receiving a portion of the scattered radiation as backscattered radiation is adapted for scanning a volume of airspace.

27. The system of claim 26 further comprising control apparatus for controlling at least one blade pitch of at least one wind turbine.

28. The system of claim 27 wherein the control and computing apparatus selectively ignores at least some of the backscattered radiation to avoid reading blade motions of at least one wind turbine as wind.

29. The system of claim 28 wherein the control and computing apparatus determines which backscattered radiation to ignore by comparing angle and range information with a location of the at least one wind turbine.

30. The system of claim 27 wherein at least a portion of the system is located within an element of a wind turbine selected from the group consisting of a nacelle and a hub.

31. The system of claim 26 wherein the control and computing apparatus is adapted for providing warning of wind conditions selected from the group consisting of hazardous wind speeds, wind shear, microbursts, and dust-devils.

32. The system of claim 26 wherein the control and computing apparatus is adapted for providing warning of atmospheric turbulence caused by events selected from the group consisting of convective instability, terrain-induced flow irregularities, obstacle-induced flow irregularities and wind forcing over rough surfaces.

33. A system for optically sensing air data comprising: a pseudorandom sequence generator for generating a pseudorandom sequence;
a tunable laser for generating laser radiation modulated by the pseudorandom sequence;
at least one beam splitter for splitting the laser radiation into a projected component and a control component;
at least one optical notch filter;
at least one control component detector coupled to receive at least a portion of the control component through the at least one optical notch filter and generate an electronic control signal therefrom;
apparatus for projecting the projected component into the air to induce scattered radiation and for receiving a portion of the scattered radiation as backscattered radiation;
at least one backscattered radiation detector coupled to receive at least a portion of the backscattered radiation through the at least one optical notch filter and generate an electronic backscatter signal therefrom; and
control and computing apparatus for sweeping a wavelength of the tunable laser, for receiving the electronic backscatter signal and the electronic control signal, for correlating the pseudorandom sequence with the electronic backscatter signal and determining Doppler shift at a plurality of ranges therefrom; and
wherein the control and computing apparatus analyzes the electronic backscatter signal to determine Rayleigh scattering, and to determine air temperature therefrom at a plurality of ranges from the system.

34. The system of claim 33 wherein the laser radiation is directed along a plurality of axes and wherein the control and computing apparatus determines wind speed and direction at a plurality of ranges from determined Doppler shift along the plurality of axes at the plurality of ranges.

35. The system of claim 34 further comprising a digital data recorder, and wherein the digital data recorder is configurable to record minimum, average, and peak-gust windspeed data with air temperature data at least four ranges from the system at least four times per hour, and wherein the digital data recorder has storage capacity for at least one month of windspeed data.

36. The system of claim 34 wherein the apparatus for projecting the projected component into the air to induce scattered radiation and for receiving a portion of the scattered radiation as backscattered radiation is adapted for scanning a volume of airspace.

37. The system of claim 36 further comprising control apparatus for controlling at least one blade pitch of at least one wind turbine.

38. The system of claim 37 wherein the control and computing apparatus filters windspeed data by comparing determined angle and range information with angle and range information corresponding to a location of at least one wind turbine to avoid reading blade motion of the at least one wind turbine as wind.

39. The system of claim 38 further comprising control apparatus for controlling at least one blade pitch of a second wind turbine.

40. The system of claim 39 wherein at least a portion of the system is located within an element of a wind turbine selected from the group consisting of a nacelle and a hub.

41. The system of claim 36 wherein the control and computing apparatus is adapted for providing warning of wind conditions selected from the group consisting of high wind speed hazards, atmospheric turbulence, wind shear, microbursts, and dust-devils in an area of interest.

42. The system of claim 36 wherein the control and computing apparatus is adapted for providing warning of the wind conditions approaching and within an aircraft approach path in the area of interest.

43. The system of claim 36 wherein the system is located near an airport, the area of interest comprises an airport traffic control and computing apparatus is adapted for providing traffic alerts when hazardous wind conditions are detected in the area of interest.

44. The system of claim 36 wherein the area of interest comprises an area near a highway, and the control and computing apparatus is adapted for providing traffic alerts when hazardous wind conditions are detected in the area of interest.

* * * * *